US009126955B2

(12) United States Patent
Kallus et al.

(10) Patent No.: US 9,126,955 B2
(45) Date of Patent: Sep. 8, 2015

(54) MACROCYCLIC UREA AND SULFAMIDE DERIVATIVES AS INHIBITORS OF TAFIA

(71) Applicant: SANOFI, Paris (FR)

(72) Inventors: Christopher Kallus, Frankfurt am Main (DE); Mark Broenstrup, Frankfurt am Main (DE); Andreas Evers, Frankfurt am Main (DE); Anja Globisch, Frankfurt am Main (DE); Herman Schreuder, Frankfurt am Main (DE); Michael Wagner, Frankfurt am Main (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/226,132

(22) Filed: Mar. 26, 2014

(65) Prior Publication Data
US 2014/0206760 A1 Jul. 24, 2014

Related U.S. Application Data

(62) Division of application No. 14/048,339, filed on Oct. 8, 2013, now Pat. No. 8,722,655, which is a division of application No. 12/996,460, filed as application No. PCT/EP2009/003650 on May 22, 2009, now Pat. No. 8,580,777.

(30) Foreign Application Priority Data

Jun. 6, 2008 (EP) ..................................... 08290520

(51) Int. Cl.
C07D 269/00 (2006.01)
C07D 413/12 (2006.01)
C07D 267/00 (2006.01)
C07D 273/01 (2006.01)
C07D 413/14 (2006.01)
C07D 273/02 (2006.01)

(52) U.S. Cl.
CPC ............ C07D 267/00 (2013.01); C07D 273/01 (2013.01); C07D 273/02 (2013.01); C07D 413/12 (2013.01); C07D 413/14 (2013.01)

(58) Field of Classification Search
CPC .............................. C07D 269/00; C07D 413/12
See application file for complete search history.

(56) References Cited

U.S. PATENT DOCUMENTS 8,580,777 B2 11/2013 Kallus et al.
2011/0178130 A1 7/2011 Kallus et al.
2014/0039011 A1 2/2014 Kallus et al.

FOREIGN PATENT DOCUMENTS

| EP | 0 611 776 A2 | 8/1994 |
|---|---|---|
| EP | 0 641 779 A1 | 3/1995 |
| WO | WO 97/30080 A1 | 8/1997 |
| WO | WO 99/11606 A2 | 3/1999 |
| WO | WO 00/44335 A2 | 8/2000 |
| WO | WO 2005/105781 A1 | 11/2005 |
| WO | WO 2008/067909 A2 | 6/2008 |

OTHER PUBLICATIONS

Aitken R.A. et al., "Synthesis and Pyrolytic Behaviour of Thiazolidin-2-One 1,1-Dioxides", J. Chem. Soc., Perkin Trans. 1:2139-2145 (1997).
Bajzar L., "Thrombin Activatable Fibrinolysis Inhibitor and an Antifibrinolytic Pathway", Arteriosclerosis, Thrombosis, and Vascular Biology 20:2511-2518 (2000).
Borghese A. et al., "Mild and Safer Preparative Method for Nonsymmetrical Sulfamides Via N-Sulfamoyloxazolidinone Derivatives: Electronic Effects Affect the Transsulfamoylation Reactivity", Organic Process Research & Development 10:770-775 (2006).
Bouma B.N. et al., "Thrombin-Activatable Fibrinolysis Inhibitor (TAFI, Plasma Procarboxypeptidase B, Procarboxypeptidase R, Procarboxypeptiase U)", Journal of Thrombosis and Haemostatis 1:1566-1574 (2003).
Carpino L.A. et al., "Advantageous Applications of Azabenzotriazole (Triazolopyridine)-Based Coupling Reagents to Solid-Phase Peptide Synthesis", J. Chem. Soc., Chem. Commun., 1994:201-203 (1994(.
Castro B. et al., "Reactifs De Couplage Peptidique IV (1)-L'Hexafluorophosphate De Benzotriazolyl N-Oxytrisdimethylamino Phosphonium (B.O.P.)", Tetrahedron Letters 14:1219-1222 (1975).
Connon S.J. et al., "Recent Developments in Olefin Cross-Metathesis", Angewandte Chemie Int. Ed. 42:1900-1923 (2003).
Dolbier Jr. W.R. et al., "Trimethylsilyl Fluorosulfonyldifluoroacetate (TFDA): A New, Highly Efficient Difluorocarbene Reagent", Journal of Fluorine Chemistry 125:459-469 (2004).
Dourtoglou V. et al., "L-Hexafluorophosphate De O-Benzotriazolyl-N,N-Tetramethyluronium: Un Reactif De Couplage Peptidique Nouveau Et Efficace", Tetrahedron Letters 15:1269-1272 (1978).
Felix A.M. et al., "Applications of BOP Reagent in Solid Phase Synthesis", Int. J. Peptide Protein Res. 31:231-238 (1988).
Ho M. et al., "A Convenient Synthesis of Chiral N-Boc-Amino Ethers as Potential Peptide Bond Surrogate Units", Tetrahedron Letters 34(41):6513-6516 (1993).
Knorr R. et al., "New Coupling Reagents in Peptide Chemistry", Tetrahedron Letters 30(15):1927-1930 (1989).

(Continued)

Primary Examiner — Bruck Kifle
(74) Attorney, Agent, or Firm — Morrison & Foerster LLP

(57) ABSTRACT

The invention relates to compounds of the formula (I) which are inhibitors of activated thrombin-activable fibrinolysis inhibitor. The compounds of the formula I are suitable for producing medicaments for prophylaxis, secondary prevention and treatment of one or more disorders associated with thromboses, embolisms, hypercoaguability or fibrotic changes.

15 Claims, No Drawings

(56) References Cited

OTHER PUBLICATIONS

Nantermet P.G. et al., "Design and Synthesis of Potent and Selective Macrocyclic Thrombin Inhibitors", Bioorganic & Medicinal Chemistry Letters 13:2781-2784 (2003).

Nicolaou K.C. et al., "Metathesis Reactions in Total Synthesis", Angewandte Chemie Int. Ed. 44(29):4490-4527 (2005).

Nicolaou I. et al., "Synthesis of N-Protected 1H-Indole-5-Carboxylic Acids With Aldose Reductase Inhibitory Potential", Organic Preparations and Procedures International: The New Journal for Organic Synthesis 34(5):511-514 (2002).

Reddy D.S. et al., "Synthesis and Conformational Studies of Dipeptides Constrained by Disubstituted 3-(Aminoethoxy)Propionic Acid Linkers", J. Org. Chem. 69:1716-1719 (2004).

Sartori G. et al., "Product Class 8: Acyclic and Cycli Ureas", Science of Synthesis 18:665-758 (2005).

Schwab P. et al., "A Series of Well-Defined Metathesis Catalysts-Synthesis of [RuC12(=CHR')(PR3)2] and Its Reactions", Angew. Chem. Int. Ed. Engl. 34(18):2039-2041 (1995).

Sheehan J.C., "A New Method of Forming Peptide Bonds", Communications to the Editor 77:1067-1068 (Feb. 20, 1955).

Simmons H.E. et al., "A New Synthesis of Cyclopropanes from Olefins", Communications to the Editor 80:5323-5324 (Oct. 5, 1958).

Trnka T.M. et al., "The Development of L2X2Ru=CHR Olefin Metathesis Catalysts: An Organometallic Success Story", Accounts of Chemical Research 34(1):18-29 (Jan. 2001).

International Search Report dated Jul. 28, 2009 received from the European Patent Office from related International Application No. PCT/EP2009/003650.

U.S. Official Action dated Jan. 28, 2014 in a related application, namely, U.S. Appl. No. 14/048,339.

MACROCYCLIC UREA AND SULFAMIDE DERIVATIVES AS INHIBITORS OF TAFIA

CROSS REFERENCE TO RELATED APPLICATIONS

This application is a divisional of U.S. application Ser. No. 14/048,339, filed Oct. 8, 2013 which is a divisional of U.S. application Ser. No. 12/996,460, filed Apr. 8, 2011, now U.S. Pat. No. 8,580,777, which is a 371 of International Application having Serial No. PCT/EP2009/003650, filed May 22, 2009 which claims benefit of European Patent Application No. 08290520.9, filed Jun. 6, 2008, which are incorporated herein by reference in their entirety.

The invention relates to novel compounds of the formula I which inhibit the enzyme TAFIa (activated thrombin-activatable fibrinolysis inhibitor), to process for their preparation and to the use thereof as medicaments.

The enzyme TAFIa is produced for example through thrombin activation from the thrombin-activatable fibrinolysis inhibitor zymogen (TAFI). The enzyme TAFI is also referred to as plasma procarboxypeptidase B, procarboxypeptidase U or procarboxypeptidase R and is a proenzyme similar to carboxypeptidase B (L. Bajzar, Arterioscler. Thromb. Vasc. Biol. 2000, pages 2511-2518).

During formation of a clot, thrombin is generated as the final product of the coagulation cascade and induces conversion of soluble plasma fibrinogen to an insoluble fibrin matrix. At the same time, thrombin activates the endogenous fibrinolysis inhibitor TAFI. Activated TAFI (TAFIa) is thus produced during thrombus formation and lysis from the zymogen TAFI through the action of thrombin; thrombomodulin in a complex with thrombin increases this effect about 1250-fold. TAFIa cleaves basic amino acids at the carboxy end of fibrin. The loss of carboxy-terminal lysines as binding sites for plasminogen then leads to inhibition of fibrinolysis. Efficient inhibitors of TAFIa prevent the loss of these high-affinity lysine binding sites for plasminogen and, in this way, assist endogenous fibrinolysis by plasmin: TAFIa inhibitors have profibrinolytic effects.

In order to maintain hemostasis in the blood, mechanisms which lead to the clotting of blood and to the breaking up of clots have developed; these are in equilibrium. If a disturbed equilibrium favors coagulation, fibrin is produced in larger quantities, so that pathological processes of thrombus formation may lead to serious pathological states in humans.

Just like excessive coagulation may lead to serious pathological states caused by thrombosis, an antithrombotic treatment entails the risk of unwanted bleeding through disturbance of the formation of a necessary hemostatic plug. Inhibition of TAFIa increases endogenous fibrinolysis—without influencing coagulation and platelet aggregation—i.e. the disturbed equilibrium is shifted in favor of fibrinolysis. It is thus possible both to counter the buildup of a clinically relevant thrombus, and to increase the lysis of a pre-existing clot. On the other hand, buildup of a hemostatic plug is not impaired, so that a hemorrhagic diathesis is probably not to be expected (Bouma et al., J. Thrombosis and Haemostasis, 1, 2003, pages 1566-1574).

Inhibitors of TAFIa have previously been described in the international application WO2005/105781.

The TAFIa inhibitors of the invention are suitable for a prophylactic and for a therapeutic use in humans suffering from disorders associated with thromboses, embolisms, hypercoaguability or fibrotic changes. They can be employed for secondary prevention and are suitable both for acute and for long-term therapy. The invention therefore relates to the use of the compound of the formula I

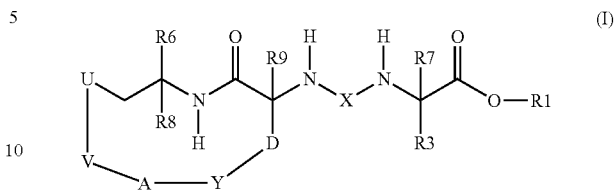

and/or of a stereoisomeric form of the compound of the formula I and/or mixtures of these forms in any ratio, and/or a physiologically tolerated salt of the compound of the formula I, where X is —C(O)— or —$SO_2$—, U is oxygen atom, sulfur atom, NH, —C(O)—NH— or —($C_0$-$C_4$)-alkylene-, A is oxygen atom, sulfur atom, NH, —C(O)—NH— —NH—C(O)—, —NR2— or —($C_0$-$C_4$)-alkylene-, V is
1) —($C_2$-$C_9$)-alkylene-, where alkylene is unsubstituted or substituted independently of one another once, twice or three times by —OH, $NH_2$ or halogen,
2) —($C_1$-$C_2$)-alkylene-($C_3$-$C_6$)-cycloalkyl-($C_1$-$C_2$)-alkylene-, where cycloalkyl is substituted independently of one another once, twice or three times by R15, or
3) —($C_3$-$C_9$)-alkenylene-, D is —($C_1$-$C_2$)-alkylene-, Y is 1) covalent bond,
2) —($C_3$-$C_{12}$)-cycloalkyl, where cycloalkyl is substituted independently of one another once, twice or three times by R15,
3) —($C_6$-$C_{14}$)-aryl, where aryl is unsubstituted or substituted independently of one another once, twice or three times by R15, or
4) Het, where Het means a 4- to 15-membered heterocyclic ring system having 4 to 15 ring atoms which are present in one, two or three ring systems which are connected together, and which comprise, depending on the ring size, one, two, three or four identical or different heteroatoms from the series oxygen, nitrogen or sulfur, and
in which Het is unsubstituted or substituted independently of one another once, twice or three times by a —($C_1$-$C_3$)-alkyl, halogen, —$NH_2$, —$CF_3$ or —O—$CF_3$, R1 is
1) hydrogen atom,
2) —($C_1$-$C_6$)-alkyl,
3) —($C_1$-$C_6$)-alkyl-OH,
4) —($C_0$-$C_4$)-alkyl-($C_3$-$C_6$)-cycloalkyl,
5) —($C_1$-$C_{10}$)-alkyl-O—C(O)—O—R2,
6) —($CH_2$)$_r$—($C_6$-$C_{14}$)-aryl, in which aryl is unsubstituted or substituted independently of one another once, twice or three times by R15, and r is the integer zero, 1, 2 or 3, or
7) —($CH_2$)$_s$-Het, where Het means a 4- to 15-membered heterocyclic ring system having 4 to 15 ring atoms which are present in one, two or three ring systems which are connected together, and which comprise, depending on the ring size, one, two, three or four identical or different heteroatoms from the series oxygen, nitrogen or sulfur, and in which Het is unsubstituted or substituted independently of one another once, twice or three times by R15, and s is the integer zero, 1, 2 or 3, R2 is 1) —($C_1$-$C_6$)-alkyl,
2) —($CH_2$)$_r$—($C_6$-$C_{14}$)-aryl, in which aryl is unsubstituted or substituted independently of one another once, twice or three times by R15, and r is the integer zero, 1, 2 or 3, or
3) —($C_0$-$C_4$)-alkyl-($C_3$-$C_6$)-cycloalkyl,
R3 is 1) —($C_2$-$C_6$)-alkylene-$NH_2$, where alkylene is unsubstituted or substituted once, twice, three or four times by halogen,
2) —($C_1$-$C_4$)-alkylene-O—($C_1$-$C_4$)-alkylene-$NH_2$,
3) —($C_1$-$C_4$)-alkylene-$SO_2$—($C_1$-$C_4$)-alkylene-$NH_2$,
4) —($C_0$-$C_4$)-alkylene-Het, where Het is as defined above and is substituted by —$NH_2$ and once, twice or three times by R15,
5) —($C_0$-$C_4$)-alkylene-($C_3$-$C_8$)-cycloalkyl-$NH_2$ or
6) —($C_0$-$C_6$)-alkylene-cyclic amine,
R6 is
1) hydrogen atom,
2) —($C_1$-$C_6$)-alkyl, where alkyl is unsubstituted or substituted independently of one another once, twice or three times by R16,
3) —O—($C_1$-$C_6$)-alkyl, where alkyl is unsubstituted or substituted independently of one another once, twice or three times by R16,
4) —($C_0$-$C_4$)-alkylene-Het, where Het is as defined above, where alkylene and Het are unsubstituted or substituted independently of one another once, twice or three times by R16,
5) —($C_0$-$C_4$)-alkylene-aryl, where alkylene and aryl are unsubstituted or substituted independently of one another once, twice or three times by R16, or
6) —($C_0$-$C_4$)-alkylene-($C_3$-$C_8$)-cycloalkyl, where alkylene and cycloalkyl are unsubstituted or substituted independently of one another once, twice or three times by R16,
R7 is hydrogen atom, halogen or —($C_1$-$C_6$)-alkyl,
R8 is hydrogen atom, halogen or —($C_1$-$C_6$)-alkyl,
R9 is hydrogen atom, halogen or —($C_1$-$C_6$)-alkyl,
R15 is hydrogen atom, —($C_1$-$C_4$)-alkyl, —O—$CF_3$, —$NH_2$, —OH, —$CF_3$ or halogen, and
R16 is —O—$CF_3$, —$NH_2$, —OH, —$CF_3$ or halogen.
2) The invention further relates to a compound of the formula I, where X is —C(O)— or —$SO_2$—,
U is oxygen atom, sulfur atom, NH, —C(O)—NH— or —($C_0$-$C_4$)-alkylene-,
A is oxygen atom, sulfur atom, NH, —C(O)—NH— or —($C_0$-$C_4$)-alkylene-,
V is
1) —($C_2$-$C_8$)-alkylene- or
2) —($C_3$-$C_8$)-alkenylene-,
D is —($C_1$-$C_2$)-alkylene-,
Y is
1) covalent bond,
2) —($C_3$-$C_{12}$)-cycloalkyl, where cycloalkyl is substituted independently of one another once, twice or three times by R15,
3) —($C_6$-$C_{14}$)-aryl, where aryl is unsubstituted or substituted independently of one another once, twice or three times by R15, or
4) Het, where Het means a 4- to 15-membered heterocyclic ring system having 4 to 15 ring atoms, which are present in one, two or three ring systems which are connected together, and which comprise, depending on the ring size, one, two, three or four identical or different heteroatoms from the series oxygen, nitrogen or sulfur, and in which Het is unsubstituted or substituted independently of one another once, twice or three times by a —($C_1$-$C_3$)-alkyl, halogen, —$NH_2$, —$CF_3$ or —O—$CF_3$, R1 is
1) hydrogen atom,
2) —($C_1$-$C_6$)-alkyl,
3) —($C_1$-$C_6$)-alkyl-OH,
4) —($C_0$-$C_4$)-alkyl-($C_3$-$C_6$)-cycloalkyl,
5) —($C_1$-$C_{10}$)-alkyl-O—C(O)—O—R2,
6) —($CH_2$)$_r$—($C_6$-$C_{14}$)-aryl, in which aryl is unsubstituted or substituted independently of one another once, twice or three times by R15, and r is the integer zero, 1, 2 or 3, or
7) —($CH_2$)$_s$-Het, where Het means a 4- to 15-membered heterocyclic ring system having 4 to 15 ring atoms which are present in one, two or three ring systems which are connected together, and which comprise, depending on the ring size, one, two, three or four identical or different heteroatoms from the series oxygen, nitrogen or sulfur, and in which Het is unsubstituted or substituted independently of one another once, twice or three times by R15, and s is the integer zero, 1 or 2 or 3,
R2 is
1) —($C_1$-$C_6$)-alkyl,
2) —($CH_2$)$_r$—($C_6$-$C_{14}$)-aryl, in which aryl is unsubstituted or substituted independently of one another once, twice or three times by R15, and r is the integer zero, 1, 2 or 3, or
3) —($C_0$-$C_4$)-alkyl-($C_3$-$C_6$)-cycloalkyl,
R3 is
1) —($C_2$-$C_6$)-alkylene-$NH_2$, where alkylene is unsubstituted or substituted once, twice, three or four times by halogen,
2) —($C_1$-$C_4$)-alkylene-O—($C_1$-$C_4$)-alkylene-$NH_2$,
3) —($C_1$-$C_4$)-alkylene-$SO_2$—($C_1$-$C_4$)-alkylene-$NH_2$,
4) —($C_0$-$C_4$)-alkylene-Het, where Het is as defined above and is substituted by —$NH_2$ and once, twice or three times by R15,
5) —($C_0$-$C_4$)-alkylene-($C_3$-$C_8$)-cycloalkyl-$NH_2$ or
6) —($C_0$-$C_6$)-alkylene-cyclic amine,
R6 is
1) hydrogen atom,
2) —($C_1$-$C_6$)-alkyl, where alkyl is unsubstituted or substituted independently of one another once, twice or three times by R16,
3) —O—($C_1$-$C_6$)-alkyl, where alkyl is unsubstituted or substituted independently of one another once, twice or three times by R16,
4) —($C_0$-$C_4$)-alkylene-Het, where Het is as defined above, where alkylene and Het are unsubstituted or substituted independently of one another once, twice or three times by R16,
5) —($C_0$-$C_4$)-alkylene-aryl, where alkylene and aryl are unsubstituted or substituted independently of one another once, twice or three times by R16, or
6) —($C_0$-$C_4$)-alkylene-($C_3$-$C_8$)-cycloalkyl, where alkylene and cycloalkyl are unsubstituted or substituted independently of one another once, twice or three times by R16,
R7 is hydrogen atom, halogen or —($C_1$-$C_6$)-alkyl,
R8 is hydrogen atom, halogen or —($C_1$-$C_6$)-alkyl,
R9 is hydrogen atom, halogen or —($C_1$-$C_6$)-alkyl,
R15 is hydrogen atom, —($C_1$-$C_4$)-alkyl, —O—$CF_3$, —$NH_2$, —OH, —$CF_3$ or halogen, and
R16 is —O—$CF_3$, —$NH_2$, —OH, —$CF_3$ or halogen.
3) The invention further relates to a compound of the formula I where X is —C(O)— or —$SO_2$—,
U is oxygen atom, sulfur atom, NH, —C(O)—NH— or —($C_0$-$C_4$)-alkylene-,
A is oxygen atom or —($C_0$-$C_4$)-alkylene-,
V is —($C_2$-$C_8$)-alkylene- or —($C_3$-$C_6$)-alkenylene-,
D is —($C_1$-$C_2$)-alkylene-,
Y is 1) covalent bond, 2) —($C_3$-$C_6$)-cycloalkyl, where cycloalkyl is substituted independently of one another once, twice or three times by R15,
3) —($C_6$-$C_{14}$)-aryl, where aryl is selected from the group of phenyl, naphthyl, anthryl or fluorenyl, and in which aryl is unsubstituted or substituted independently of one another once, twice or three times by R15, or
4) Het, where Het is selected from the group of acridinyl, azepinyl, azetidinyl, aziridinyl, benzimidazalinyl, benzimidazolyl, benzo[1,3]dioxolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]tetrahydrofuranyl, dihydrofuranyl, dioxolyl, dioxanyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pryidooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienoimidazolyl, thienooxazolyl, thienopyridine, thienothiazolyl, thiomorpholinyl, thiophenyl, triazinyl, 1,2,3-triazolyl, 1,2,3-triazolyl, 1,2,4-triazolyl, 1,2,5-triazolyl, 1,3,4-triazolyl and xanthenyl, and
in which Het is unsubstituted or substituted independently of one another once, twice or three times by a —($C_1$-$C_3$)-alkyl, halogen, —$NH_2$, —$CF_3$ or —O—$CF_3$,
R1 is
1) hydrogen atom or
2) —($C_1$-$C_4$)-alkyl,
R3 is
1) —($C_2$-$C_6$)-alkylene-$NH_2$, where alkylene is unsubstituted or substituted once, twice, three or four times by halogen,
2) —($C_1$-$C_4$)-alkylene-$SO_2$—($C_1$-$C_4$)-alkylene-$NH_2$ or
3) —($C_0$-$C_4$)-alkylene-Het, where Het is as defined above and is substituted by —$NH_2$ and once, twice or three times by R15,
R6 is
1) hydrogen atom,
2) —($C_1$-$C_6$)-alkyl, where alkyl is unsubstituted or substituted independently of one another once, twice or three times by R16,
3) —O—($C_1$-$C_6$)-alkyl, where alkyl is unsubstituted or substituted independently of one another once, twice or three times by R16,
4) —($C_0$-$C_4$)-alkylene-Het, where Het is as defined above, where alkylene and Het are unsubstituted or substituted independently of one another once, twice or three times by R16,
5) —($C_0$-$C_4$)-alkylene-aryl, where alkylene and aryl are unsubstituted or substituted independently of one another once, twice or three times by R16, or
6) —($C_0$-$C_4$)-alkylene-($C_3$-$C_6$)-cycloalkyl, where alkylene and cycloalkyl are unsubstituted or substituted independently of one another once, twice or three times by R16,
R7 is hydrogen atom, F or —($C_1$-$C_4$)-alkyl,
R8 is hydrogen atom, F or —($C_1$-$C_4$)-alkyl,
R9 is hydrogen atom, F or —($C_1$-$C_4$)-alkyl,
R15 is hydrogen atom, —($C_1$-$C_4$)-alkyl, —O—$CF_3$, —$NH_2$, —OH, —$CF_3$ or halogen, and
R16 is —O—$CF_3$, —OH, —$CF_3$ or F.
4) The invention further relates to a compound of the formula I where X is —C(O)—,
U is oxygen atom,
A is oxygen atom or —($C_0$-$C_4$)-alkylene-,
V is
1) —($C_2$-$C_8$)-alkylene-, where alkylene is unsubstituted or substituted independently of one another once or twice by —OH, F or Cl,
2) —($C_1$-$C_2$)-alkylene-cyclopropyl-($C_1$-$C_2$)-alkylene-, where cyclopropyl is substituted once or twice by F, or
3) —($C_3$-$C_6$)-alkenylene-,
D is —($C_1$-$C_2$)-alkylene-,
Y is 1) covalent bond or
2) phenyl, in which phenyl is unsubstituted or substituted independently of one another once, twice or three times by R15,
R1 is
1) hydrogen atom or
2) —($C_1$-$C_4$)-alkyl,
R3 is
1) —($C_2$-$C_6$)-alkylene-$NH_2$,
2) —($C_1$-$C_4$)-alkylene-$SO_2$—($C_1$-$C_4$)-alkylene-$NH_2$ or
3) —($C_0$-$C_4$)-alkylene-pyridyl, where pyridyl is substituted by —$NH_2$ and once, twice or three times by R15,
R6 is
1) hydrogen atom,
2) —($C_1$-$C_6$)-alkyl,
3) —$CF_3$,
4) —($C_0$-$C_4$)-alkylene-phenyl or
5) —($C_0$-$C_4$)-alkylene-($C_3$-$C_6$)-cycloalkyl,
R7, R8 and R9 are each hydrogen atom, and
R15 is hydrogen atom, —($C_1$-$C_4$)-alkyl, —$CF_3$ or halogen.
5) The invention further relates to a compound of the formula I where
X is —C(O)—,
U is oxygen atom,
A is oxygen atom or —($C_0$-$C_4$)-alkylene-,
V is —($C_2$-$C_8$)-alkylene- or —($C_3$-$C_6$)-alkenylene-,
D is —($C_1$-$C_2$)-alkylene-,
Y is
1) covalent bond or
2) phenyl, in which phenyl is unsubstituted or substituted independently of one another once, twice or three times by R15,
R1 is
1) hydrogen atom or
2) —($C_1$-$C_4$)-alkyl,
R3 is
1) —($C_2$-$C_6$)-alkylene-$NH_2$,
2) —($C_1$-$C_4$)-alkylene-$SO_2$—($C_1$-$C_4$)-alkylene-$NH_2$ or
3) —($C_0$-$C_4$)-alkylene-pyridyl, where pyridyl is substituted by —$NH_2$ or once, twice or three times by R15, R6 is
1) hydrogen atom,
2) —($C_1$-$C_6$)-alkyl,
3) —$CF_3$,
4) —($C_0$-$C_4$)-alkylene-phenyl or
5) —($C_0$-$C_4$)-alkylene-($C_3$-$C_6$)-cycloalkyl,
R7, R8 and R9 are each hydrogen atom, and
R15 is hydrogen atom, —($C_1$-$C_4$)-alkyl, —$CF_3$ or halogen.

The term "($C_1$-$C_6$)-alkyl" means hydrocarbon radicals whose carbon chain is straight-chain or branched and comprises 1 to 6 carbon atoms, for example methyl, ethyl, propyl, isopropyl, butyl, isobutyl, tertiary butyl, pentyl, isopentyl, neopentyl, hexyl, 2,3-dimethylbutane or neohexyl.

The term "—($C_0$-$C_4$)-alkylene-" means hydrocarbon radicals whose carbon chain is straight-chain or branched and comprises 1 to 4 carbon atoms, for example methylene, ethylene, propylene, isopropylene, isobutylene, butylene or tertiary butylene. "—$C_0$-Alkylene" is a covalent bond.

The term "—($C_3$-$C_9$)-alkylene-" means hydrocarbon radicals whose carbon chain is straight-chain or branched and comprises 3 to 9 carbon atoms, for example propylene, isopropylene, butylene, isobutylene, pentylene, isopentylene, neopentylene, hexylene, 2,3-dimethylbutanylene, neohexylene, heptylene, octanylene or nonanylene.

The term "—($C_3$-$C_9$)-alkenylene" means hydrocarbon radicals whose carbon chain is straight-chain or branched and comprises 3 to 9 carbon atoms and have, depending on the chain length, 1, 2 or 3 double bonds, for example ethenylene, propenylene, isopropenylene, isobutenylene or butenylene; the substituents on the double bond may, where possible in principle, be disposed in E or Z positions.

The term "($C_3$-$C_{12}$)-cycloalkyl" means radicals such as compounds derived from 3- to 12-membered mono-, bi- or tricycles or bridged rings such as the monocycles cyclopropane, cyclobutane, cyclopentane, cyclohexane, cycloheptane or cyclooctane, derived from the bicycles bicyclo[4.2.0]octane, octahydroindene, decahydronaphthalene, decahydroazulene, decahydrobenzocycloheptene or dodecahydroheptalene, or from tricycles such as adamantane, or derived from the bridged rings such as spiro[2.5]octane, spiro[3.4]octane, spiro[3.5]nonane, bicyclo[3.1.1]heptane, bicyclo[2.2.1]heptane, bicyclo[2.2.2]octane or octahydro-4,7-methanindene.

The term "—($C_6$-$C_{14}$)-aryl" means aromatic carbon radicals having 6 to 14 carbon atoms in the ring. Examples of —($C_6$-$C_{14}$)-aryl radicals are phenyl, naphthyl, for example 1-naphthyl, 2-naphthyl, 1,2,3,4-tetrahydronaphthalenyl, anthryl or fluorenyl. Naphthyl radicals and especially phenyl radicals are preferred aryl radicals.

The term "4- to 15-membered heterocyclic ring system" or "Het" means ring systems having 4 to 15 ring atoms which are present in one, two or three ring systems connected together and which comprise, depending on the ring size, one, two, three or four identical or different heteroatoms from the series oxygen, nitrogen or sulfur. Examples of these ring systems are the radicals acridinyl, azepinyl, azetidinyl, aziridinyl, benzimidazalinyl, benzimidazolyl, benzo[1,3]dioxol, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]-tetrahydrofuranyl, dihydrofuranyl, dioxolyl, dioxanyl, 2H,6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pryidooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienoimidazolyl, thienooxazolyl, thienopyridine, thienothiazolyl, thiomorpholinyl, thiophenyl, triazinyl, 1,2,3-triazolyl, 1,2,3-triazolyl, 1,2,4-triazolyl, 1,2,5-triazolyl, 1,3,4-triazolyl and xanthenyl. Preferred Het rings are the radicals isoxazolyl, benzo[1,3]dioxole, thiophenyl, imidazole and thiazole.

The term "halogen" means fluorine, chlorine, bromine or iodine, preferably fluorine, chlorine or bromine, especially chlorine or bromine.

The term "—$SO_2$-" means a sulfonyl radical.
The term "—C(O)—" means a carbonyl radical.
The term "cyclic amines" means ring systems such as cyclic amines, for example azetidinyl, pyrrolidinyl, piperidinyl, piperazinyl, azepinyl, morpholinyl or thiomorpholinyl.

The invention further relates to a process for preparing the compound of the formula I, which comprises
a) reacting a compound of the formula (II)

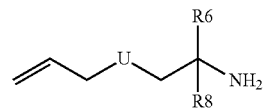

(II)

where U, R6 and R8 have the meanings mentioned in the compound of the formula (I), with an amino acid of the formula (III)

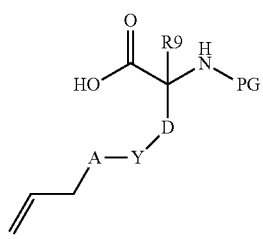

(III)

in which R9, A, Y and D have the meanings mentioned in the compound of the formula (I), resulting in a compound of the formula (IV)

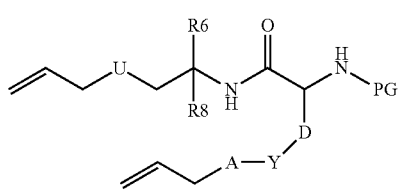

(IV)

which is converted under the conditions of ring-closure metathesis and subsequent hydrogenation of the resulting double bond into a compound of the formula (V)

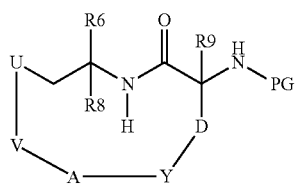

(V)

where V is —(C$_2$-C$_9$)-alkylene- or —(C$_3$-C$_9$)-alkenylene-, subsequently eliminating the protective group PG, and obtaining the compound of the formula (VI),

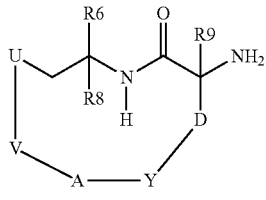

(VI)

and reacting with a compound of the formula (VII)

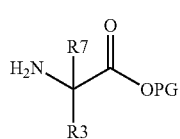

(VII)

in which R3 and R7 have the meanings mentioned in formula (I), PG is a suitable ester protective group radical, and the nitrogen in R3 is protected where appropriate by a suitable amino protective group, with phosgene or a phosgene equivalent to give a compound of the formula (VIII)

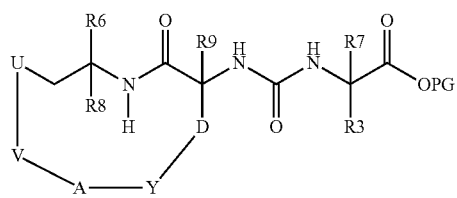

(VIII)

subsequently the protective group PG and the protective group which is present where appropriate on the nitrogen in R3 are eliminated, resulting in the compound of the formula (I), or b) reacting a compound of the formula (IX)

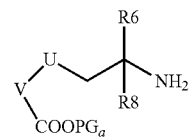

(IX)

in which U, V, R6 and R8 have the meanings mentioned in the compound of the formula (I), and PG$_a$ is a suitable carboxyl protective group, with an amino acid of the formula (X)

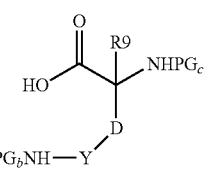

(X)

in which R9, Y and D have the meanings mentioned in the compound of the formula I, and PG$_b$ and PG$_c$ are suitable amino protective groups, resulting in a compound of the formula (XI)

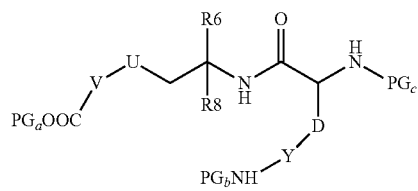

(XI)

which, after elimination of the protective groups PG$_a$ and PG$_b$, is converted into the compound of the formula (XII)

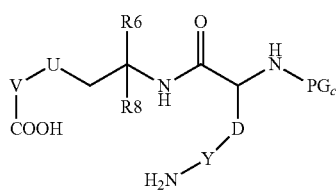

(XII)

which is converted by means of an amide coupling into a compound of the formula (V),
in which A has the meanings mentioned in the compound of the formula I, subsequently the protective group is eliminated and the compound of the formula (VI) is obtained,
and reacted with a compound of the formula (VII)
in which R3 and R7 have the meanings mentioned in formula I, PG is a suitable ester protective group radical, and the nitrogen in R3 is protected where appropriate by a suitable amino protective group, with phosgene or a phosgene equivalent to give a compound of the formula (VIII), subsequently the protective group PG and the protective group which is present where appropriate on the nitrogen in R3 are eliminated, resulting in the compound of the formula (I), or c) reacting a compound of the formula (XIII)

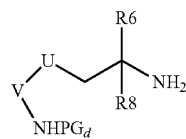
(XIII)

in which U, V, R6 and R8 have the meanings mentioned in the compound of the formula I, and $PG_d$ is a suitable amino protective group, with an amino acid of the formula (XIV)

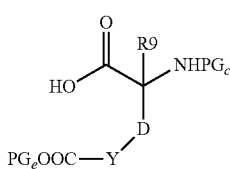
(XIV)

in which R9, Y and D have the meanings mentioned in the compound of the formula I, and $PG_c$ is a suitable amino protective group and $PG_e$ is a suitable carboxyl protective group, resulting in a compound of the formula (XV)

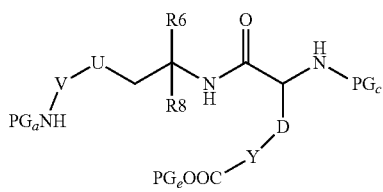
(XV)

which, after elimination of the protective groups $PG_d$ and $PG_e$, is converted into the compound of the formula (XVI)

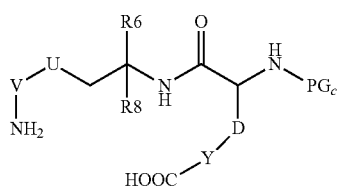
(XVI)

which is reacted to give a compound of the formula (V),
in which A has the meanings mentioned in the compound of the formula I,
subsequently the protective group is eliminated and the compound of the formula (VI) is obtained,
and reacted with a compound of the formula (VII),
in which R3 and R7 have the meanings mentioned in formula I, PG is a suitable ester protective group radical, and the nitrogen in R3 is protected where appropriate by a suitable amino protective group, with phosgene or a phosgene equivalent to give a compound of the formula (VIII), subsequently the protective group PG and the protective group which is present where appropriate on the nitrogen in R3 are eliminated, resulting in the compound of the formula (I), or d) reacting a compound of the formula XVII

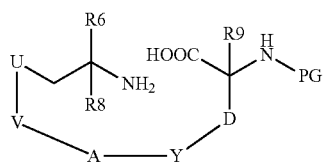
(XVII)

in which U, V, A, Y, D, $R_6$, $R_8$ and $R_9$ have the meanings mentioned in the compound of the formula I, with a compound of the formula (V), subsequently the protective groups are eliminated, and a compound of the formula (VI) is obtained, and reacted with a compound of the formula (VII), in which R3 and R7 have the meanings mentioned in formula I, PG is a suitable ester protective group radical, and the nitrogen in R3 is protected where appropriate by a suitable amino protective group, with phosgene or a phosgene equivalent to give a compound of the formula (VIII), and subsequently the protective groups PG and, where appropriate, the protective group on the nitrogen in R3 are eliminated, resulting in the compound of the formula (I), or e) converting a compound of the formula (VIIIa)

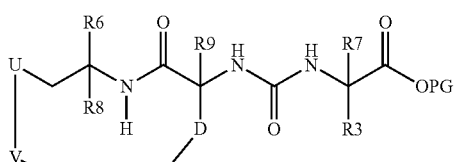
(VIIIa)

in which V is —$(C_3-C_9)$-alkenylene-, into the compound of the formula (VIIIb)

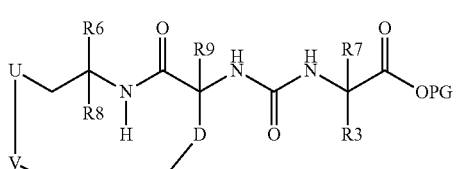
(VIIIb)

in which V is —$(C_3-C_9)$-alkylene-, where alkylene is substituted independently of one another once, twice or three times by —OH, $NH_2$ or halogen, or is —$(C_1-C_2)$-alkylene-$(C_3-C_6)$-cycloalkyl-$(C_1-C_2)$-alkylene-, where cycloalkyl is substituted independently of one another once, twice or three times by R15, subsequently the compound of the formula (VIIIb) is converted in analogy to process a) into the compound of the formula (I), or f) reacting a compound of the formula (XVIII)

(XVIII)

in which V is as defined in the compound of the formula (I), successively with the compounds of the formula (XIX) and (XX)

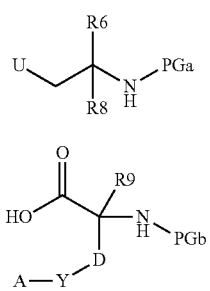

(XIX)

(XX)

employing bases in polar, aprotic solvents, and converting the resulting compounds of the formula (XXI)

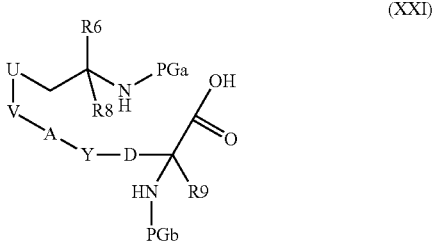
(XXI)

by removing the protective group PGa and subsequent formation of a peptide linkage into a compound of the formula (V), and reacting the latter as in process a) to give compounds of the formula (I) in which R6, R8, R9, and A, D, U, V and Y have the meanings mentioned in formula (I), and PG is suitable protective groups, and LG is a leaving group such as chlorine, bromine, iodine or sulfonic ester, or g) reacting a compound of the formula VI with a compound of the formula (XXII)

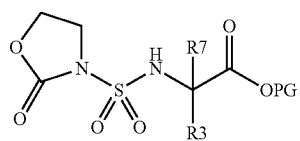
(XXII)

in which R3 and R7 have the meanings mentioned in the compound of the formula I, and PG is a suitable protective group radical, to give a compound of the formula (XXIII)

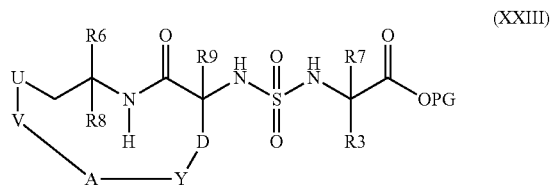
(XXIII)

and then converting into a compound of the formula (I), or h) fractionating a compound of the formula I prepared by processes a), b), c), d), e), f) or g), or a suitable precursor of the formula (I) which occurs in enantiomeric forms owing to its chemical structure, by salt formation with enantiopure acids or bases, chromatography on chiral stationary phases or derivatization by means of chiral enantiopure compounds such as amino acids, separation of the diastereomers obtained in this way, and elimination of the chiral auxiliary groups into the pure enantiomers, or i) either isolating in free form the compound of the formula (I) prepared by processes a), b), c), d), e), f) or g), or converting into physiologically tolerated salts in the case where acidic or basic groups are present.

The preparation options described in processes a) to f) may be varied in the sequence of the process steps and are not confined to the processes described in this way; thus, for example, the urea or sulfamide linkage can first be formed to give compounds of the type XII (depicted here for the urea type), subsequently deprotected and reacted with a compound of type II to give compounds of type XIV, which then afford the compounds I of the invention in analogy to VIII and further.

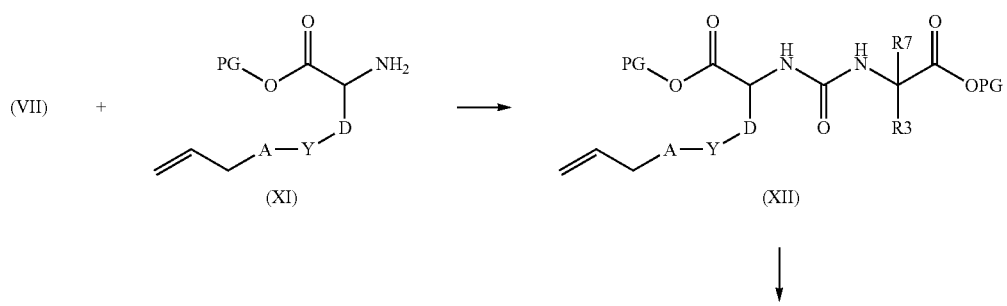

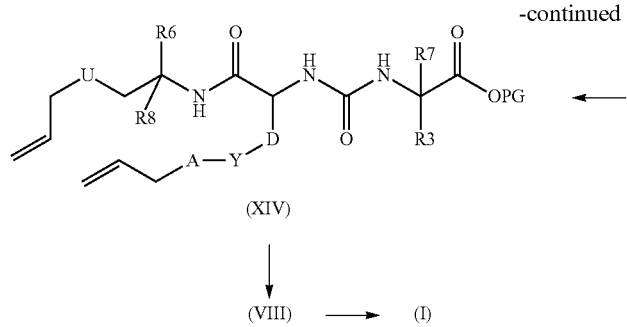

(XIV) → (XIII)

(VIII) → (I)

Preparation of compounds of type II is for example by direct allylation of commercially available amino alcohols using allylating agents such as allyl halides or allyl sulfonic esters in polar aprotic solvents such as tetrahydrofuran (THF) or dimethylformamide (DMF) employing strong bases such as sodium hydride, lithium hexamethyldisilazane or alkali metal carbonates described in Organic Preparations and Procedures International, 34 (5) 511-514. Alternatively, the amino group can previously be protected, for example by formation of the Schiff's bases as described in Journal of the Chemical Society, Perkin Transactions 1: Organic and Bio-Organic Chemistry, (14), 2139-2145; 1997. Removal of the protective group can take place in acidic media, preferably dilute hydrochloric acid, in water-soluble organic solvents such as THF or methanol or mixtures of a plurality of such solvents. Compounds of type III are commercially available or can be obtained from commercially available amino acid derivatives as described above by allylation on an atom, preferably on a heteroatom of the side chain.

Compounds of type VII are commercially available or can be obtained by standard processes of protective group chemistry (see below).

Compounds of type IX can be prepared by standard processes of organic chemistry, such as by Michael addition of substituted β-amino alcohols onto α,β-unsaturated ester compounds in the presence of catalytic amounts of sodium (J. Org. Chem. Vol. 69, No. 5, 2004, 1716-1719)

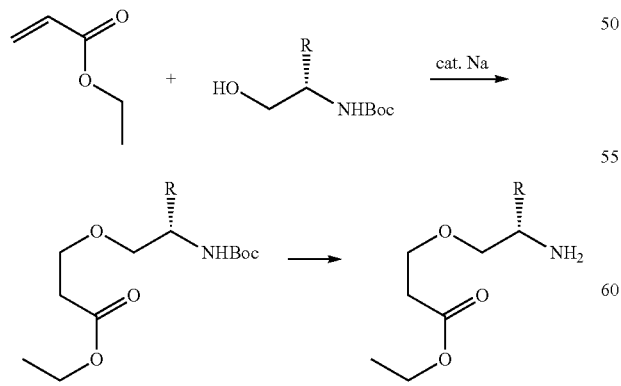

or else by Lewis acid-catalyzed addition of appropriately substituted alcohols onto protected aziridines

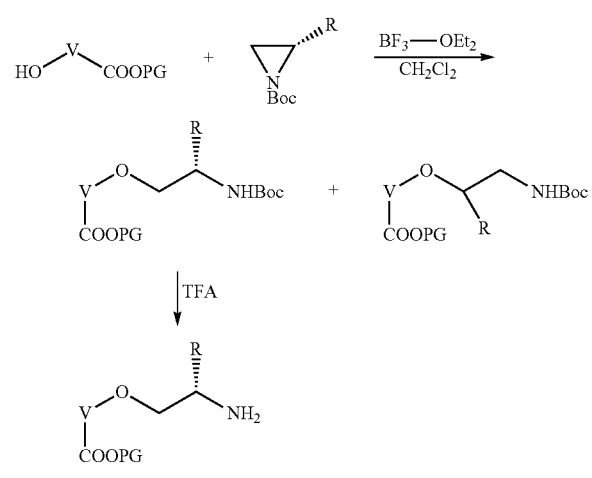

Compounds of type X are ordinarily commercially available, such as

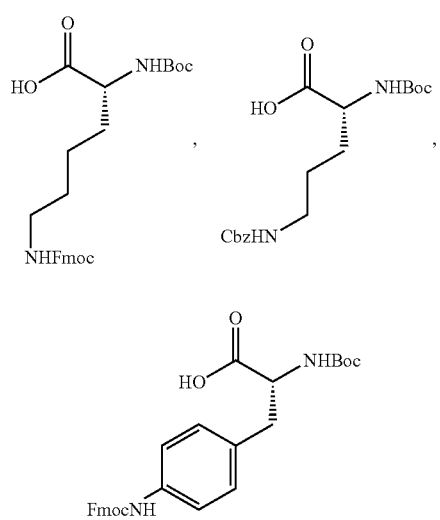

or can be prepared therefrom by standard transformations.

Likewise, compounds of type XIV are ordinarily commercially available, such as

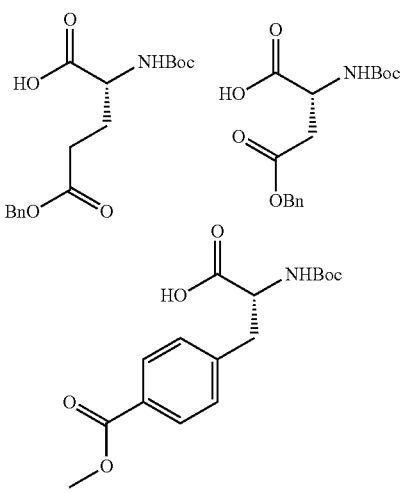

or can be prepared therefrom by standard transformations.

Compounds of type XIII can be obtained, as described above, by Lewis acid-catalyzed addition of appropriate amino alcohols onto protected substituted aziridines

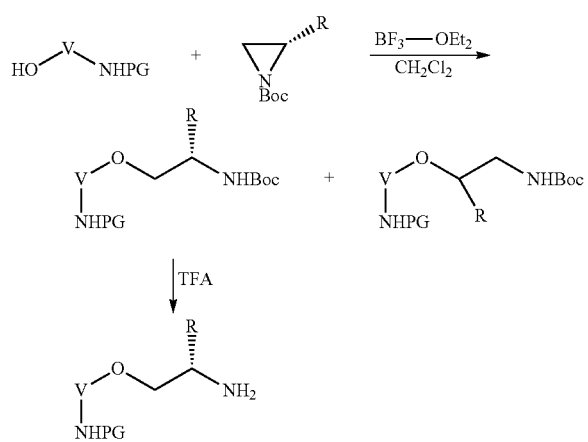

as described in Tetrahedron Letters, Vol. 34, No. 41, 1993, 6513-6516. Preparation of 2-oxooxazolidine-3-sulfonamides of type XVIII and subsequent conversion into sulfamides is described for example in Organic Process Research & Development (2006), 10(4), 770-775 and can be undertaken here from known amino acid derivatives.

Methods for peptide coupling are described for instance in Bodanszky (M. Bodanszky, Principles of Peptide Synthesis, 2nd ed, Springer, Berlin, 1993). Mention may be made for example from the diversity of known methods of the activations of carboxylic acids by the carbodiimide process (J. Am. Chem. Soc., 1955, 77, 1067) and by active ester processes such as, for example, by phosphonium salts (Tetrahedron Lett., 1975, 14; Int, J. Peptide Protein Res. 1988, 31, 231) or uronium salts (Tetrahedron Lett., 1978, 1269, Tetrahedron Lett. 1989, 30, 1927, J. Chem. Soc., Chem. Commun. 1994, 201). Protective groups, the introduction, elimination and stability thereof are described for example in Greene (T. W. Greene, P. G. M. Wuts, Protective Groups in Organic Synthesis, 3rd ed, Wiley, New York, 1999). Preferred protective groups are for example amino protective groups such as tert-butyloxycarbonyl, fluorenyloxycarbonyl, benzyloxycarbonyl, benzylidene or diphenylmethylidene protective groups; preferred carboxyl protective groups are alkyl esters such as methyl, ethyl, benzyl or silyl esters such as trimethylsilyl esters. The preparation of ureas is described in detail for example in G. Sartori; R. Maggi, Acyclic and cyclic ureas Science of Synthesis (2005), 18, 665-758. The two amino components are in this case reacted in polar or nonpolar aprotic solvents such as DMF, dichloromethane, acetonitrile, where appropriate with the addition of a base such as alkali metal carbonate or organic nitrogen bases, preferably triethylamine or diisopropylethylamine and, where appropriate, an acylation catalyst such as dimethylaminopyridine, with phosgene, triphosgene, diphosgene or phosgene equivalents such as 1,1'-carbonyldiimidazole or disuccidinyl carbonate or chloroformic esters to form activated urea precursors. Formation of the urea linkage can also take place by using the appropriate isocyanates of one of the two coupling partners. Ring closure metathesis (olefin metathesis) means the ring-closing carbon-carbon linkage between two alkenyl groups through the action of the metallocarbene catalysts of Grubbs, Hoyveda-Grubbs or Schrock in solvents such as, for example, dichloromethane, benzene, pentane or THF with elimination of ethylene, preferably at temperatures between 25 and 50° C., and is described for example in Angew. Chem., Int. Ed. Engl. 1995, 34, 2039-2041; Acc. Chem. Res. 2001, 34, 18-29; Handbook of Metathesis, Grubbs, R. H. Ed., Wiley-VCH, Weinheim, Germany, 2003; Angew. Chem. Int. Ed. 2003, 42, 1900-1923; Angew. Chem., Int. Ed. 2005, 44, 4490-4527. Hydrogenation means the well-known transfer of hydrogen to unsaturated carbon-carbon bond in suitable solvents such as lower alcohols, ethers and esters through the action of a hydrogen atmosphere and use of transition metals as catalyst. These and further modifications of carbon multiple bonding such as hydroboration, oxymercuration and epoxidation are described in detail for example in Organikum, Wiley-VCH, 22nd edition, pages 288 et seq. Dihydroxylation of a double bond can be carried out for example by a Sharpless dihydroxylation with conversion of a carbon multiple bond into 1,2-diols using an osmium catalyst, a stoichiometric oxidizing agent such as $K_3Fe(CN)_6$ in a buffer, where appropriate with the addition of chiral ligands or premade mixtures such as AD-Mix in suitable solvents. Cyclopropanations are carried out on carbon multiple bonds by employing carbene sources in inert solvents such as ethers, for example by the method of Simmons-Smith (dihalomethane and zinc/copper couple) or Furukawa (dihalomethane and diethylzinc) as described for example in J. Am. Chem. Soc., 1958, 80, 5323-5324; difluorocyclopropanations can be carried out as described in J. Fluorine Chem. 2004, 125, 459, for example by heating with trimethylsilyl fluorosulfonyldifluoroacetate and catalytic amounts of fluoride without diluent or in inert high-boiling solvents.

Amino acid derivatives having a sulfone group in the side chain can be obtained for example by oxidizing the corresponding cysteine derivatives or other sulfur-containing side chains in inert solvents with oxidizing agents such as, for example, oxone or m-chloroperbenzoic acid.

Amino acid derivatives having a Het-alkylidene radical in the side chain are either commercially available or can be obtained by alkylation as shown in the following scheme under conditions as described above for the allylation,

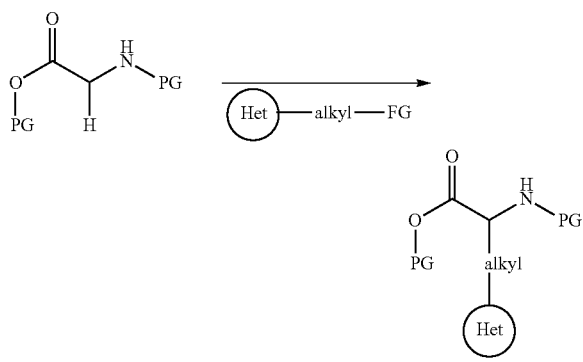

where FG is a suitable leaving group such as halogen or sulfonic ester and PG is a suitable protective group. The enantiomers of these amino acids can be obtained for example by chiral chromatography. Alternatively, the derivatives can be obtained by condensation of the heterocyclic aldehydes with amino acids or aminomalonic acid derivatives, where appropriate with the addition of mineral acids or organic acid catalysts or dehydrating agents such as orthoformic esters or inorganic sulfates and subsequent hydrogenation, where appropriate with chiral hydrogenation catalysts

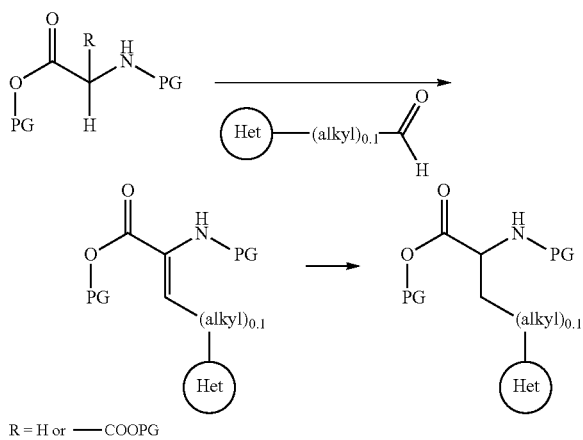

R = H or —COOPG where PG is a suitable protective group.

A compound of the formula I prepared by these processes, or a suitable precursor of the formula I which occurs in enantiomeric form owing to its chemical structure, can be fractionated by salt formation with enantiopure acids or bases, chromatography on chiral stationary phases or derivatization by means of chiral enantiopure compounds such as amino acids, separation of the diastereomers obtained in this way, and elimination of the chiral auxiliary groups into the pure enantiomers (process b), or the compound of the formula I prepared as in Scheme 1 or 3 can either be isolated in free form or be converted into physiologically tolerated salts in the case where acidic or basic groups are present (process d).

In process step h), the compound of the formula I, if it occurs as mixture of diastereomers or enantiomers, or results as mixtures thereof in the chosen synthesis, is separated into the pure stereoisomers, either by chromatography on an optionally chiral support material or, if the racemic compound of the formula I is able to form salts, by fractional crystallization of the diastereomeric salts formed with an optically active base or acid as auxiliary. Examples of suitable chiral stationary phases for thin-layer or column chromatographic separation of enantiomers are modified silica gel supports (called Pirkle phases) and high molecular weight carbohydrates such as triacetylcellulose. For analytical purposes it is also possible to use gas chromatography methods, after appropriate derivatization known to the skilled worker, on chiral stationary phases. To separate enantiomers of the racemic carboxylic acids, diastereomeric salts differing in solubility are formed with an optically active, usually commercially available base such as (−)-nicotine, (+)- and (−)-phenylethylamine, quinine bases, L-lysine or L- and D-arginine, the less soluble component is isolated as solid, the more soluble diastereomer is deposited from the mother liquor, and the pure enantiomers are obtained from the diastereomeric salts obtained in this way. It is possible in the same way in principle to convert the racemic compounds of the formula I comprising a basic group such as an amino group with optically active acids such as (+)-camphor-10-sulfonic acid, D- and L-tartaric acid, D- and L-lactic acid, and (+) and (−)-mandelic acid into the pure enantiomers. Chiral compounds comprising alcohol or amine functions can also be converted with appropriately activated or optionally N-protected enantiopure amino acids into the corresponding esters or amides, or conversely chiral carboxylic acids can be converted with carboxy-protected enantiopure amino acids into the amides, or with enantiopure hydroxy carboxylic acids such as lactic acid into the corresponding chiral esters. The chirality of the amino acid or alcohol residue introduced in enantiopure form can then be utilized for separating the isomers by carrying out a separation of the diastereomers now present by crystallization or chromatography on suitable stationary phases, and then eliminating the included chiral moiety again by suitable methods.

A further possibility with some of the compounds of the invention is to employ diastereomerically or enantiomerically pure starting materials to prepare the framework structures. It is thus possible where appropriate also to employ other or simplified processes for purifying the final products. These starting materials have previously been prepared enantiomerically or diastereomerically pure by processes known from the literature. This may mean in particular that either enantioselective processes are employed in the synthesis of the basic structures, or else a separation of enantiomers (or diastereomers) is carried out at an early stage of the synthesis and not at the stage of the final products. A simplification of these separations can likewise be achieved by proceeding in two or more stages.

Acidic or basic products of the compound of the formula I may be in the form of their salts or in free form. Pharmacologically acceptable salts are preferred, for example alkali metal or alkaline earth metal salts such as hydrochlorides, hydrobromides, sulfates, hemisulfates, all possible phosphates, and salts of amino acids, natural bases or carboxylic acids.

Physiologically tolerated salts are prepared from compounds of the formula I able to form salts, including their stereoisomeric forms, in step h) of the process in a manner known per se. The compounds of the formula I form stable alkali metal, alkaline earth metal or, where appropriate, substituted ammonium salts with basic reagents such as hydroxides, carbonates, bicarbonates, alcoholates and ammonia or organic bases, for example trimethyl- or triethylamine, ethanolamine, diethanolamine or triethanolamine, trometamol or else basic amino acids, for example lysine, ornithine or arginine. If the compounds of the formula I have basic groups, it is also possible to prepare stable acid addition salts with strong acids. Suitable for this purpose are both inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic, or trifluoroacetic acid.

The invention also relates to medicaments characterized by an effective content of at least one compound of the formula I and/or of a physiologically tolerated salt of the compound of the formula I and/or an optionally stereoisomeric form of the compound of the formula I, together with a pharmaceutically suitable and physiologically tolerated carrier, additive and/or further active ingredients and excipients.

By reason of the pharmacological properties, the compounds of the invention are suitable for the prophylaxis, secondary prevention and therapy of all disorders which can be treated by inhibition of TAFIa. Thus, TAFIa inhibitors are suitable both for a prophylactic and for a therapeutic use in humans. They are suitable both for an acute treatment and for a long-term therapy. TAFIa inhibitors can be employed in patients suffering from impairments of wellbeing or diseases associated with thromboses, embolisms, hypercoaguability or fibrotic changes. These include myocardial infarction, angina pectoris and all other forms of acute coronary syndrome, stroke, peripherally vascular disorders, deep vein thrombosis, pulmonary embolism, embolic or thrombotic events caused by cardiac arrhythmias, cardiovascular events such as restenosis following revascularization, angioplasty and similar procedures such as stent implantations and bypass operations. TAFIa inhibitors can additionally be employed in all procedures leading to contact of the blood with foreign surfaces such as, for example, for dialysis patients and patients with indwelling catheters. TAFIa inhibitors can be employed to reduce the risk of thrombosis after surgical procedures such as operations on the knee and hip joints.

TAFIa inhibitors are suitable for the treatment of patients with disseminated intravascular coagulation, sepsis and other intravascular events associated with inflammation. TAFIa inhibitors are additionally suitable for the prophylaxis and treatment of patients with atherosclerosis, diabetes and the metabolic syndrome and the sequalae thereof. Impairments of the hemostatic system (e.g. fibrin deposits) have been implicated in mechanisms leading to tumor growth and tumor metastasis, and for inflammatory and degenerative articular disorders such as rheumatoid arthritis and arthrosis. TAFIa inhibitors are suitable for slowing down or preventing such processes.

Further indications for the use of TAFIa inhibitors are fibrotic changes of the lung such as chronic obstructive pulmonary disease, adult respiratory distress syndrome (ARDS) and of the eye such as fibrin deposits following eye operations. TAFIa inhibitors are also suitable for the prevention and/or treatment of scarring.

The medicaments of the invention can be administered by oral, inhalational, rectal or transdermal administration or by subcutaneous, intraarticular, intraperitoneal or intravenous injection. Oral administration is preferred. It is possible for stents and other surfaces which come into contact with blood in the body to be coated with TAFIa inhibitors.

The invention also relates to a process for producing a medicament, which comprises making a suitable dosage form from at least one compound of the formula I with a pharmaceutically suitable and physiologically tolerated carrier and, where appropriate, further suitable active ingredients, additives or excipients.

Suitable solid or pharmaceutical formulations are, for example, granules, powder, coated tablets, tablets, (micro) capsules, suppositories, syrups, solutions, suspensions, emulsions, drops or injectable solutions, and products with protracted release of active ingredient, in the production of which conventional aids such as carriers, disintegrants, binders, coating agents, swelling agents, glidants or lubricants, flavorings, sweeteners and solubilizers are used. Excipients which are frequently used and which may be mentioned are magnesium carbonate, titanium dioxide, lactose, mannitol and other sugars, talc, milk protein, gelatin, starch, cellulose and its derivatives, animal and vegetable oils such as fish liver oil, sunflower, peanut or sesame oil, polyethylene glycol and solvents such as, for example, sterile water and monohydric or polyhydric alcohols such as glycerol.

The pharmaceutical products are preferably produced and administered in dosage units, where each unit comprises as active ingredient a particular dose of the compound of the invention of the formula I. In the case of solid dosage units such as tablets, capsules, coated tablets or suppositories, this dose can be up to about 1000 mg, but preferably about 50 to 300 mg and, in the case of injection solutions in ampoule form, up to about 300 mg but preferably about 10 to 100 mg.

The daily doses indicated for the treatment of an adult patient weighing about 70 kg are, depending on the activity of the compound of formula I, from about 2 mg to 1000 mg of active ingredient, preferably about 50 mg to 500 mg. However, in some circumstances, higher or lower daily doses may also be appropriate. The daily dose can be administered either by a single administration in the form of a single dosage unit or else a plurality of smaller dosage units or by multiple administration of divided doses at particular intervals.

TAFIa inhibitors can be administered both as monotherapy and in combination or together with all antithrombotics (anticoagulants and platelet aggregation inhibitors), thrombolytics (plasminogen activators of every type), other substances having profibrinolytic activity, antihypertensives, regulators of blood glucose, lipid-lowering agents and antiarrhythmics.

EXAMPLES

Final products are normally determined by mass spectroscopic methods (FAB-, ESI-MS) and $^1$H-NMR; the main peak or two main peaks are indicated in each case. Temperatures are stated in degrees Celsius, RT means room temperature (21° C. to 24° C.). TFA means trifluoroacetic acid, THF means tetrahydrofuran, DMF means dimethylformamide, HATU means 2-(7-aza-1H-benzotriazol-1-yl)-1,1,3,3-tetramethyluronium hexafluorophosphate, HOAt means 1-hydroxy-7-azabenzotriazole. Abbreviations used are either explained or correspond to usual conventions.

Unless stated otherwise, the LC/MS analyses were carried out under the following conditions:

Method A: =method column: YMC Jsphere H80 20×2 mm, packing material 4 μm, mobile phase: $CH_3CN:H_2O+0.05\%$ trifluoroacetic acid (TFA), gradient: 4:96 (0 min.) to 95:5 (2.0 min.) to 95:5 (2.4 min.) to 4:96 (2.45 min.) flow rate: 1.0 ml/min., temperature: 30° C.

Method B: column: Phenomenex $LunaC_{18}$ 10×2.0 mm, packing material 3 μm, mobile phase: $CH_3CN:H_2O+0.05\%$ TFA, gradient: 7:93 (0 min) to 95:5 (1.2 min) to 95:5 (1.4 min) to 7:93 (1.45 min), flow rate: 1.1 ml/min, temperature: 30° C.

Method C: column: WatersXBridge$C_{18}$, 4.6*50 mm, 2.5 μm, gradient: $H_2O+0.05\%$ TFA:$CH_3CN+0.05\%$ TFA 95:5 (0 min) to 95:5 (0.3 min) to 5:95 (3.5 min) to 5:95 (4 min), flow rate: 1.3 ml/min, temperature: 40° C.

Method D: column: Waters XBridge $C_{18}$ 4.6*50 mm; 2.5 μm gradient: $H_2O$+0.1% formic acid:$CH_3CN$+0.08% formic acid 97:3 (0 min) to 40:60 (3.5 min) to 2:98(4 min) to 2:98(5 min) to 97:3 (5.2 min) to 97:3 (6.5 min), flow rate: 1.4 ml/min, temperature: RT.

Method E: column: YMC Jsphere 33*2 mm, 4 μm, H80, gradient: $H_2O$+0.05% TFA:$CH_3CN$+0.05% TFA 98:2 (1 min) to 5:95 (5.0 min) to 5:95 (6.25 min), flow rate: 1 ml/min, temperature: RT.

Method F: column: WatersXBridge$C_{18}$, 4.6*50 mm, 2.5 μm, gradient: $H_2O$+0.1% formic acid:$CH_3CN$+0.1% formic acid 97:3 (0 min) to 40:60 (3.5 min) to 2:98 (4 min) to 2:98 (5 min) to 97:3 (5.2 min) to 97:3 (6.5 min), temperature: RT.

Method G: column: WatersXBridge$C_{18}$, 4.6*50 mm, 2.5 μm; gradient: $H_2O$+0.05% TFA:$CH_3CN$+0.05% TFA 95:5 (0 min) to 95:5 (0.2 min) to 5:95 (2.4 min) to 5:95 (3.5 min) to 95:5 (3.6 min) to 95:5 (4.5 min), flow rate: 1.7 ml/min, temperature: 50° C.

Method H: column WatersXBridge$C_{18}$, 4.6*50 mm, 2.5 μm; gradient: $H_2O$+0.05% TFA:$CH_3CN$+0.05% TFA 95:5 (0 min) to 95:5 (0.2 min) to 5:95 (2.4 min) to 5:95 (3.2 min) to 95:5 (3.3 min) to 95:5 (4.0 min), flow rate: 1.7 ml/min, temperature: 40° C.

Method I: column Merck Chromolith FastGrad RP-18e, 50×2 mm; gradient: $H_2O$+0.05% TFA:$CH_3CN$+0.05% TFA 98:2 (0.2 min) to 2:98 (2.4 min) to 2:98 (3.2 min) to 98:2 (3.3 min) to 98:2 (4 min), flow rate: 2.0 ml/min, temperature: RT.

Method J: column: YMC Jsphere 33*2 mm, 4 μm, gradient: $H_2O$+0.05% TFA:$CH_3CN$+0.05% TFA 98:2 (1 min) to 5:95 (5.0 min) to 5:95 (6.25 min), flow rate: 1 ml/min, temperature: RT.

Method K: column YMC Jsphere 33*2 mm, 4 μm, H80, gradient: $H_2O$+0.05% TFA:$CH_3CN$+0.05% TFA 96:4 (0 min) to 5:95 (2.0 min) to 5:95 (2.4 min) to 96:4 (2.45 min).

Method L: column YMC Jsphere 33*2 mm, 4 μm, gradient: $CH_3OH$+0.05% TFA: $H_2O$+0.05% TFA 2:98 (1 min) to 95:5 (5 min) to 95:5 (6.25 min), flow rate: 1 ml/min, temperature: RT.

Unless indicated otherwise, chromatographic separations were carried out on silica gel with ethyl acetate/heptane mixtures as mobile phase. Preparative separations on reversed phase (RP) silica gel (HPLC) were carried out, unless indicated otherwise, on C18-RP phases as stationary phase and $H_2O$-TFA-acetonitrile mixtures as mobile phase.

Evaporation of solvents normally took place under reduced pressure in a rotary evaporator at 35° C. to 45° C.

Example 1-1

(S)-6-Amino-2-[3-((9S,12R)-9-isopropyl-11-oxo-2, 7-dioxa-10-azabicyclo[12.2.2]octadeca-1(17),14(18), 15-trien-12-yl)ureido]hexanoic acid

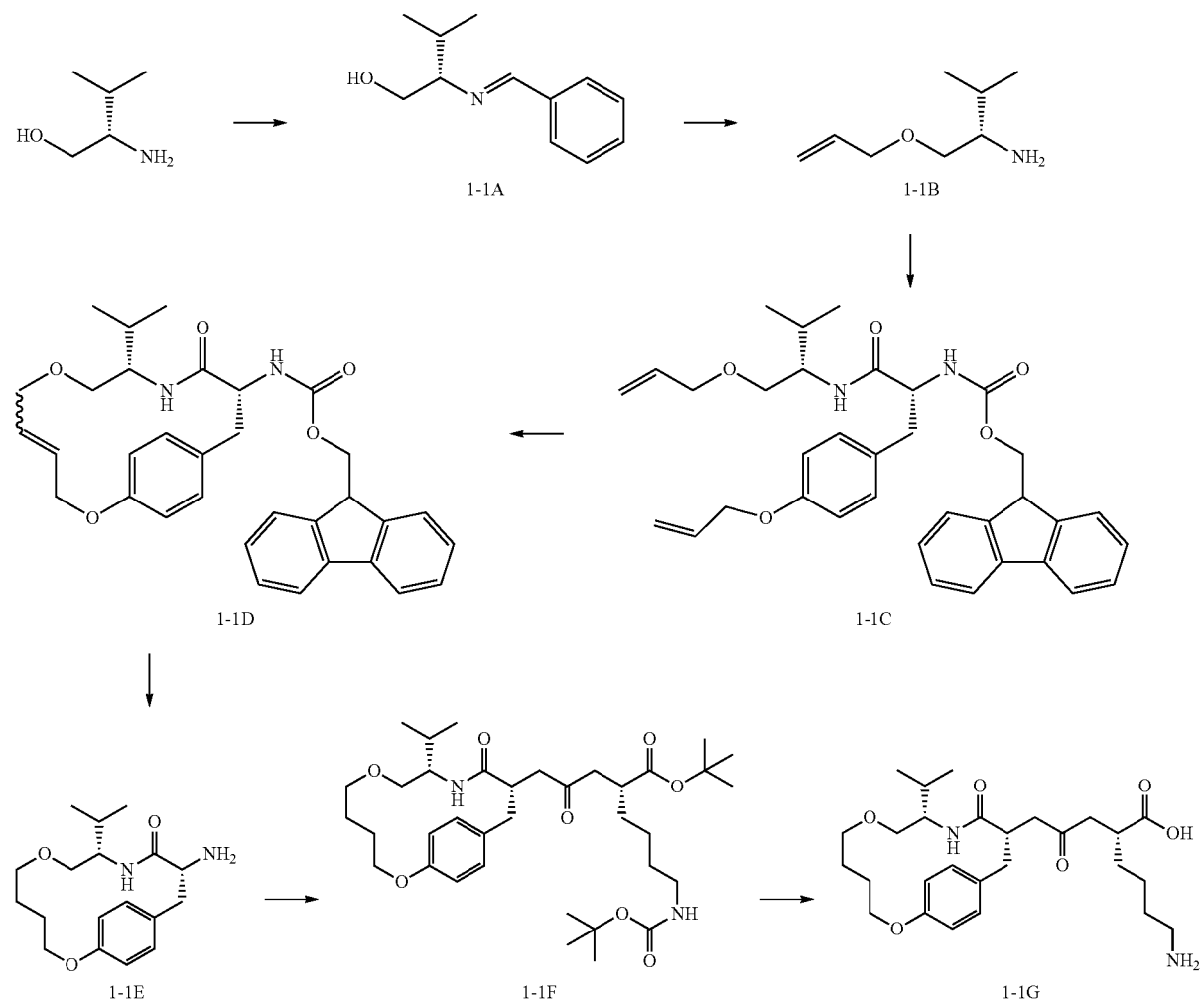

A. (S)-3-Methyl-2-{[1-phenylmethylidene]amino}butan-1-ol 2.64 ml (2.78 g, 26.16 mmol) of benzaldehyde were added to a stirred solution of 2.57 g (24.91 mmol) of L-valinol in 28 ml of toluene, and the mixture was heated under reflux with a water trap for one hour. Cooling was followed by concentration and recrystallization from heptane. The colorless solid was filtered off with suction and dried under reduced pressure (3.74 g).

$^1$H-NMR (DMSO-d$_6$, 400 MHz) δ [ppm]=8.23 (s, 1H), 7.77 (d, 2H), 7.45-7.40 (m, 3H), 4.49 (t, 1H), 3.68-3.31 (m, 1H), 3.48-3.40 (m, 1H), 2.96 (ddd, 1H), 1.94-1.81 (m, 1H), 0.88 (s, 5H).

B. (S)-1-Allyloxymethyl-2-methylpropylamine 1.25 g (60%, 31.36 mmol) of sodium hydride were added to a solution of 3.00 g (15.68 mmol) of (S)-3-methyl-2-{[1-phenylmethylidene]amino}butan-1-ol in 28 ml of dry THF, and the mixture was stirred at RT for 45 min. Then 1.43 ml (16.46 mmol) of allyl bromide were added, and the mixture was stirred further at RT overnight. 20 ml of methanol were added to quench, and the mixture was acidified (pH 1) with 1N hydrochoric acid and stirred further. After 3 h, the reaction mixture was washed twice with dichloromethane, and the combined dichloromethane phases were extracted with 1N hydrochloric acid. The combined aqueous phases were basified with 1N sodium hydroxide solution (pH 14), saturated with sodium chloride and extracted three times with ethyl acetate, readjusting the pH after each extraction step. The combined organic phases were dried over sodium sulfate, filtered and concentrated, and taken up once in dichloromethane and again concentrated. 1.56 g of the title compound were obtained as a pale yellow liquid.

LC/MS (method A): R$_t$=0.68 min, m/z: 144.2 [MH$^+$].

C. 9H-Fluoren-9-ylmethyl[(R)-1-((S)-1-allyloxymethyl-2-methylpropylcarbamoyl)-2-(4-allyloxyphenyl)ethyl]carbamate 25.74 g (58.04 mmol) of (R)-3-(4-allyloxyphenyl)-2-(9H-fluoren-9-ylmethoxycarbonylamino)propionic acid were introduced into 400 ml of THF and, after successive addition of 8.88 g (58.04 mmol) of N-hydroxybenzotriazole and 11.98 g (58.04 mmol) of N,N'-dicyclohexylcarbodiimide, stirred at RT. After leaving the mixture to stand overnight it was filtered and concentrated. The residue was taken up in ethyl acetate and washed successively with saturated sodium bicarbonate solution and dilute hydrochloric acid. The organic phase was dried over sodium sulfate and concentrated, and the residue was separated by chromatography on silica gel. 13.55 g of the desired compound were obtained.

LC/MS (method A): R$_t$=1.95 min, m/z: 569.3 [MH$^+$].

D. 9H-Fluoren-9-ylmethyl((9S,12R)-9-isopropyl-11-oxo-2,7-dioxa-10-azabicyclo[12.2.2]octadeca-1(17),4,14(18),15-tetraen-12-yl)carbamate A solution of 1.25 g (2.20 mmol) of 9H-fluoren-9-ylmethyl[(R)-1-(S)-1-allyloxymethyl-2-methylpropylcarbamoyl)-2-(4-allyloxyphenyl)ethyl]carbamate and 0.40 g (0.659 mmol) of dichloro(o-isopropoxyphenylmethylene)(tricyclohexylphosphine)ruthenium (Hoyveda-Grubbs catalyst) in 610 ml of dichloromethane was stirred at 40° C. for 24 h. The reaction mixture was then concentrated, and the residue was purified by chromatography on silica gel. 1.03 g of the desired compound were obtained as a colorless solid.

LC/MS (method A): R$_t$=1.75 min, m/z: 541.3 [MH$^+$].

E. (9S,12R)-12-Amino-9-isopropyl-2,7-dioxa-10-azabicyclo[12.2.2]octadeca-1(17),14(18),15-trien-11-one A mixture of 6.82 g (12.62 mmol) of 9H-fluoren-9-ylmethyl((9S,12R)-9-isopropyl-11-oxo-2,7-dioxa-10-azabicyclo[12.2.2]octadeca-1(17),4,14(18),15-tetraen-12-yl)-carbamate and 4.4 g of 10% Pd/C in 880 ml of methanol was stirred under a hydrogen atmosphere at RT. After 6 h, it was filtered and freed of solvent. The residue was separated by preparative HPLC. The required fractions were combined, acetonitrile was evaporated off, and the resulting aqueous solution was made slightly alkaline with sodium bicarbonate. The aqueous phase was extracted several times with ethyl acetate, and the combined organic phases were dried over sodium sulfate, filtered and concentrated. Chromatography on silica gel with ethyl acetate/methanol mixtures afforded the title compound (2.90 g).

LC/MS (method A): R$_t$=1.02 min, m/z: 321.2 [MH$^+$].

F. tert-Butyl (S)-6-tert-butoxycarbonylamino-2-[3-(9S,12R)-9-isopropyl-11-oxo-2,7-dioxa-10-azabicyclo[12.2.2]octadeca-1(17),14(18),15-trien-12-yl)ureido]hexanoate A solution of 1.59 g (4.68 mmol) of tert-butyl (S)-2-amino-6-tert-butoxycarbonylaminohexanoate hydrochloride, 1.43 ml (1.04 g, 10.30 mmol) of triethylamine and 0.76 g (4.68 mmol) of carbonyldiimidazole in 25 ml of dimethylformamide (DMF) was stirred at RT for 1 h and then a solution of 1.5 g in 20 ml of DMF was added. The mixture was stirred at RT and left to stand overnight. Evaporation of the solvent was followed by partition between ethyl acetate and water, and the organic phase was dried over sodium sulfate, filtered and concentrated. The residue was separated by preparative HPLC, and the required fractions were combined and freed of acetonitrile. Sodium bicarbonate was used to make slightly alkaline, and the mixture was extracted with ethyl acetate. The combined organic phases were dried over sodium sulfate, filtered and concentrated. 0.73 g of the title compound was obtained.

LC/MS (method A): R$_t$=1.68 min, m/z: 649.4 [MH$^+$].

G. (S)-6-Amino-2-[3-((9S,12R)-9-isopropyl-11-oxo-2,7-dioxa-10-azabicyclo[12.2.2]octadeca-1(17),14(18),15-trien-12-yl)ureido]hexanoic acid 0.71 g (1.10 mmol) of tert-butyl (S)-6-tert-butoxycarbonylamino-2-[3-((9S,12R)-9-isopropyl-11-oxo-2,7-dioxa-10-azabicyclo[12.2.2]octadeca-1 (17),14(18),15-trien-12-yl) ureido]hexanoate was dissolved in 11 ml of dichloromethane, and the same volume of trifluoroacetic acid was added. Stirring at RT for 4 h was followed by concentration and fractionation of the residue by preparative HPLC. The required fractions were combined and, after evaporation of acetonitrile, mixed with dilute hydrochloric acid, concentrated further and finally freeze dried. 0.42 g of the title compound was obtained as hydrochloride.

$^1$H-NMR (DMSO-d$_6$, 400 MHz) δ [ppm]=7.79 (3H, s, br), 7.22 (1H, d), 6.99-6.90 (m, 3H), 6.87 (d, 1H), 6.29 (d, 1H), 5.79 (d, 1H), 4.32-4.17 (m, 3H), 4.10 (dd, 1H), 3.29-3.18 (m, 3H), 3.12 (dd, 1H), 2.96-2.87 (m, 2H), 2.83-2.72 (m, 2H), 2.65 (dd, 1H), 1.78-1.2 (m, 11H), 0.72 (d, 3H), 0.67 (d, 2H); LC/MS (method A): $R_t$=0.94 min, m/z: 493.4 [MH$^+$].

The following examples were obtained in an analogous manner by employing the appropriate amino alcohols instead of valinol:

| Example | Name | $R_t$ (min) | m/z [MH$^+$] | Method |
|---|---|---|---|---|
| 1-2 | (S)-6-Amino-2-[3-((R)-11-oxo-2,7-dioxa-10-azabicyclo[12.2.2]octadeca-1(17),14(18),15-trien12-yl)ureido]hexanoic acid | 0.77 | 451.4 | A |
| 1-3 | (S)-6-Amino-2-[3-((R)-9,9-dimethyl-11-oxo-2,7-dioxa-10-azabicyclo[12.2.2]octadeca-1(17),14(18),15-trien-12-yl)ureido]hexanoic acid | 0.93 | 479.2 | A |
| 1-4 | (S)-6-Amino-2-[3-((9S,12R)-11-oxo-9-phenyl-2,7-dioxa-10-azabicyclo[12.2.2]octadeca-1(17),14(18),15-trien-12-yl)ureido]hexanoic acid | 0.96 | 527.5 | A |
| 1-5 | (S)-6-Amino-2-[3-((9S,12R)-9-benzyl-11-oxo-2,7-dioxa-10-azabicyclo[12.2.2]octadeca-1(17),14(18),15-trien-12-yl)ureido]hexanoic acid | 1.03 | 541.3 | A |
| 1-6 | (S)-6-Amino-2-[3-((9S,12R)-9-cyclohexyl-11-oxo-2,7-dioxa-10-azabicyclo[12.2.2]octadeca-1(17),14(18),15-trien-12-yl)ureido]hexanoic acid | 1.02 | 533.3 | A |
| 1-7 | (S)-6-Amino-2-[3-((9S,12R)-9-ethyl-11-oxo-2,7-dioxa-10-azabicyclo[12.2.2]octadeca-1(17),14(18),15-trien-12-yl)ureido]hexanoic acid | 2.26 | 479.26 | C |
| 1-8 | (S)-6-Amino-2-[3-((9S,12R)-9-methyl-11-oxo-2,7-dioxa-10-azabicyclo[12.2.2]octadeca-1(17),14(18),15-trien-12-yl)ureido]hexanoic acid | 2.21 | 465.25 | C |
| 1-9 | (S)-6-Amino-2-[3-((9S,12R)-9-tert-butyl-11-oxo-2,7-dioxa-10-azabicyclo[12.2.2]octadeca-1(17),14(18),15-trien-12-yl)ureido]hexanoic acid | 2.39 | 507.33 | E |
| 1-10 | (S)-6-Amino-2-{3-[(9S,12R)-9-((S)-sec-butyl)-11-oxo-2,7-dioxa-10-azabicyclo[12.2.2]octadeca-1(17),14(18),15-trien-12-yl]ureido}hexanoic acid | 2.41 | 507.24 | C |

Example 2-1

(S)-6-Amino-2[3-((13S,16R)-13-isopropyl-15-oxo-2,11-dioxa-14-azabicyclo[16.2.2]docosa-1(21),18(22),19-trien-16-yl)ureido]hexanoic acid A. (R)-1-(2-Hept-6-enyloxymethyl)-2-methylpropylamine A solution of 3.00 g (15.68 mmol) of (S)-3-methyl-2-{[1-phenylmethylidene]amino}butan-1-ol (1-1A) was prepared in 28 ml of dry THF under argon, 1.50 g (60%, 37.51 mmol) of sodium hydride were added, and the mixture was stirred for 45 min. Addition of 2.83 g (15.68 mmol) of 7-bromohept-1-ene was followed by stirring further overnight, cautious quenching with 20 ml of methanol, subsequent addition of 300 ml of 1N hydrochloric acid (pH=1) and stirring at 40° C. for 2 h. The mixture was washed with dichloromethane, and the aqueous phase was adjusted to pH 14 with 1N sodium hydroxide solution and extracted three times with ethyl acetate. The combined organic phases were dried over sodium sulfate, filtered and concentrated. 0.91 g of the crude product was obtained. The crude product was reacted further without further purification.

LC/MS (method B): $R_t$=0.72 min, m/z: 200.2 [MH$^+$].

B. 9H-Fluoren-9-yl-methyl[(R)-2-(4-allyloxyphenyl)-1-(S)-1-hept-6-enyloxymethyl-2-methylpropylcarbamoyl)ethyl]carbamate A solution of 2.02 g (4.57 mmol) of N-α-(9-fluorenylmethyloxycarbonyl)-O-allyl-D-tyrosine in 46 ml of DMF was mixed with 0.77 g (5.02 mmol) of 1-hydroxybenzotriazole and 1.04 g (5.02 mmol) of N,N'-dicyclohexylcarbodiimide and stirred at RT for 2 h. Then 0.91 g (4.57 mmol) of (R)-1-(2-hept-6-enyloxymethyl)-2-methylpropylamine was added, and the mixture was stirred further at RT and left to stand overnight. The precipitate was then filtered off, the filtrate was concentrated, the residue was taken up in ethyl acetate and washed successively with saturated sodium bicarbonate solution and dilute hydrochloric acid, and the organic phase was dried over sodium sulfate, filtered and concentrated. The residue was separated by preparative HPLC, and the required fractions were combined, freed of acetonitrile and extracted with ethyl acetate. The organic phase was dried over sodium sulfate, filtered and concentrated. 1.02 g of the title compound were obtained (method D): $R_t$=5.49 min, m/z: 669 [M-H+HCOOH$^-$].

C. 9H-Fluoren-9-yl-methyl((13S,16R)-13-isopropyl-15-oxo-2,11-dioxa-14-azabicyclo[16.2.2]docosa-1(21),4,18(22),19-tetraen-16-yl)carbamate A solution of 1.01 g (1.61 mmol) of 9H-fluoren-9-yl-methyl[(R)-2-(4-allyloxyphenyl)-1-((S)-1-hept-6-enyloxymethyl-2-methylpropylcarbamoyl)ethyl]carbamate and 0.15 g (0.24 mmol) of dichloro(o-isopropoxyphenylmethylene)(tricyclohexylphosphine)ruthenium (Hoyveda-Grubbs catalyst) in 460 ml of dichloromethane was stirred at 40° C. for 24 h. The reaction mixture was then concentrated, and the residue was purified by chromatography on silica gel. 0.87 g of the desired compound was obtained as a colorless solid.

LC/MS (method C): $R_t$=4.30 min, m/z: 597.39 [MH$^+$].

D. (13S,16R)-16-Amino-13-isopropyl-2,11-dioxa-14-azabicyclo[16.2.2]docosa-1(21),18(22),19-trien-15-one A mixture of 0.87 (1.46 mmol) of 9H-fluoren-9-yl-methyl ((13S,16R)-13-isopropyl-15-oxo-2,11-dioxa-14-azabicyclo [16.2.2]docosa-1(21),4,18(22),19-tetraen-16-yl)-carbamate and 0.16 g of 10% Pd/C in 100 ml of methanol was stirred under a hydrogen atmosphere at RT. After stirring overnight and addition of 0.5 ml of piperidine, stirring was continued for 2 h, and the mixture was filtered and freed of solvent. The residue was separated by preparative HPLC. The required fractions were combined and freeze dried. 0.18 g of the title compound was obtained as trifluoroacetate.

LC/MS (method C): $R_t$=3.07 min, m/z: 377.22 [MH$^+$].

E. (S)-6-Amino-2-[3-((13S,16R)-13-isopropyl-15-oxo-2,11-dioxa-14-azabicyclo[16.2.2]docosa-1(21),18(22),19-trien-16-yl)ureido]hexanoic acid A solution of 0.18 g (0.37 mmol) of (13S,16R)-16-amino-13-isopropyl-2,11-dioxa-14-azabicyclo[16.2.2]docosa-1(21),18(22),19-trien-15-one in 3.8 ml of DMF was added to 60 mg (0.37 mmol) of 1,1'-carbonyldiimidazole and, after addition of 0.2 ml (0.15 g, 1.47 mmol) of triethylamine, stirred under argon. After 10 min, 124 mg (0.37 mmol) of tert-butyl (S)-2-amino-6-tert-butoxycarbonylaminohexanoate hydrochloride were added, and the mixture was stirred for 3 h. It was concentrated and partitioned between water and ethyl acetate, and the organic phase was dried over sodium sulfate, filtered and concentrated. The residue was purified by preparative HPLC. The required fractions were combined and concentrated. The residue was taken up in 20 ml of dichloromethane/TFA (1:1, v/v) and left to stand for 2 h. The mixture was concentrated, dissolved in 1N hydrochloric acid with a little acetonitrile and freeze dried. An amorphous solid (0.12 g) was obtained as hydrochloride.

LC/MS (method C): $R_t$=2.88 min, m/z: 549.21 [MH$^+$].

Example 3-1

(S)-6-Amino-2-[3-((E)-(9S,12R)-9-isopropyl-11-oxo-2,7-dioxa-10-azabicyclo[12.2.2]octadeca-1(17),4,14(18),15-tetraen-12-yl)ureido]hexanoic acid The title compound was obtained in analogy to Example 1-1 with omission of the hydrogenation step and without final freeze drying with hydrochloric acid directly as trifluoroacetate.

LC/MS (method A): $R_t$=0.89 min, m/z: 491.2 [MH$^+$].

Example 4-1

(S)-6-Amino-2-[3-((3S,6R)-3-isopropyl-5-oxo-1-oxa-4-azacyclotetradec-6-yl)ureido]hexanoic acid The title compound was obtained in analogy to Example 2-1 using Fmoc-D-allylglycine instead of Fmoc-D-O-allyltyrosine.

LC/MS (method C): $R_t$=2.35 min, m/z: 443.34 [MH$^+$].

The following were obtained in the same way using other amino alcohols and, where appropriate, using or introducing an ester protective group:

| Example | Name | $R_t$ (min) | m/z [MH$^+$] | Method |
|---|---|---|---|---|
| 4-2 | (S)-3-(6-Aminopyridin-3-yl)-2-[3-((3S,6R)-3-isopropyl-5-oxo-1-oxa-4-azacyclotetradec-6-yl)ureido]propionic acid | 2.52 | 478.27 | H |
| 4-3 | (S)-3-(6-Aminopyridin-3-yl)-2-[3-((3S,6R)-3-methyl-5-oxo-1-oxa-4-azacyclotetradec-6-yl)ureido]propionic acid | 1.66 | 450.26 | G |
| 4-4 | Ethyl (S)-3-(6-aminopyridin-3-yl)-[3-((3S,6R)-3-isopropyl-5-oxo-1-oxa-4-azacyclotetradec-6-yl)ureido]propionate | 0.66 | 506.4 | B |
| 4-5 | Ethyl (S)-3-(6-amino-pyridin-3-yl)-2-[3-((3S,6R)-3-methyl-5-oxo-1-oxa-4-azacyclotetradec-6-yl)ureido]propionate | 1.81 | 478.37 | G |

Example 5-1

(R)-3-(2-Aminoethanesulfonyl)-2-[3-((9S,12R)-9-isopropyl-11-oxo-2,7-dioxa-10-azabicyclo[12.2.2]octadeca-1(17),14(18),15-trien-12-yl)ureido]propionic acid

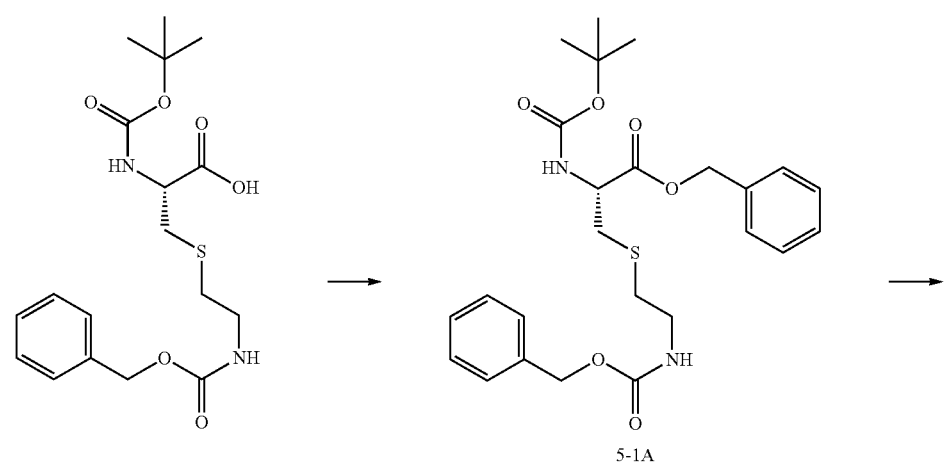

5-1A

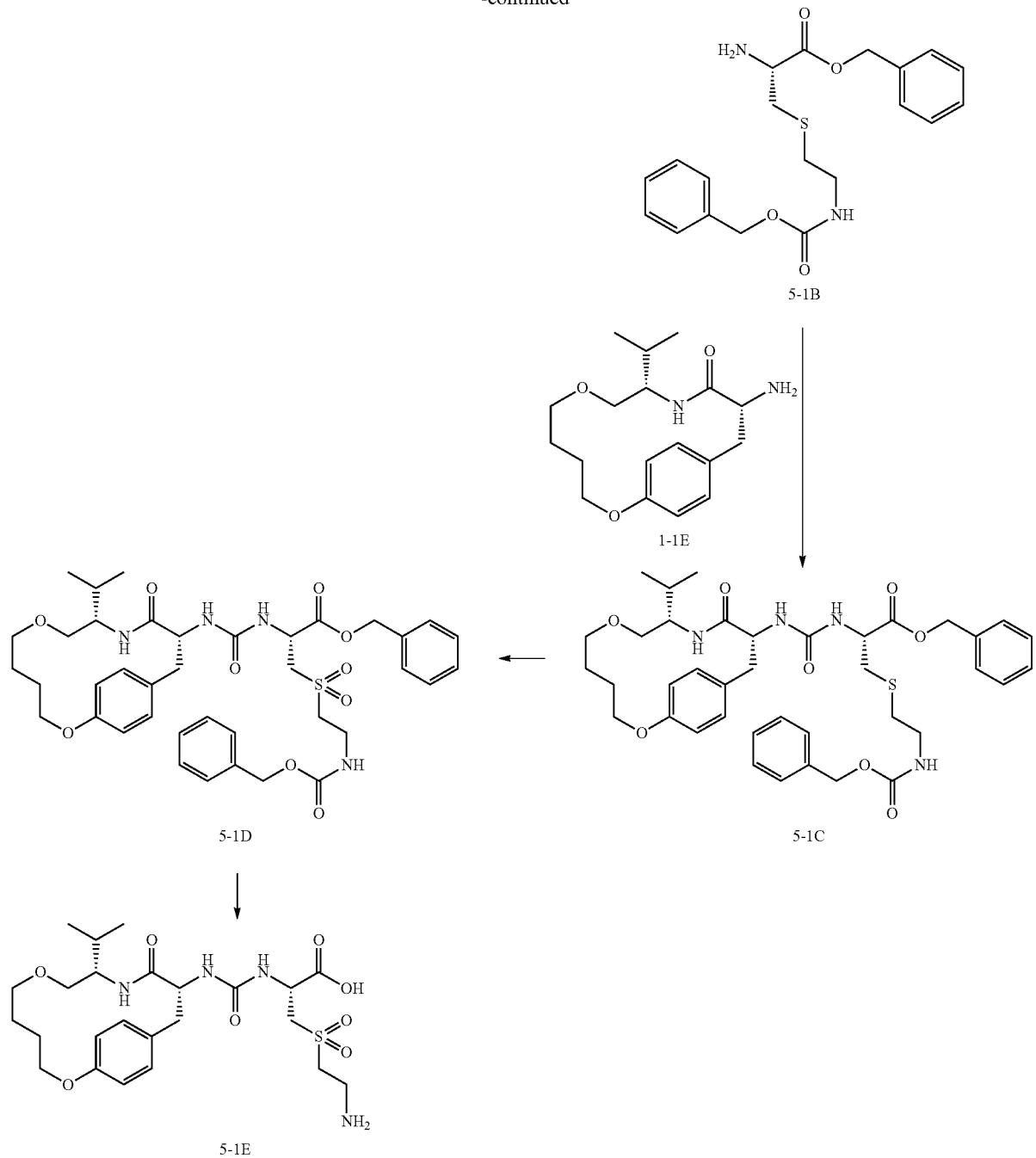

A. Benzyl(R)-3-(2-benzyloxycarbonylaminoethyl-sulfanyl)-2-tert-butoxycarbonylaminopropionate A solution of 2.30 g (5.77 mmol) of (R)-3-(2-benzyloxycarbonylaminoethylsulfanyl)-2-tert-butoxycarbonylaminopropionic acid, 0.60 ml (0.62 g, 5.77 mmol) of benzyl alcohol, 0.07 g (0.58 mmol) of 4-dimethylaminopyridine and 1.33 g (6.93 mmol) of N-(3-dimethylaminopropyl)-N'-ethylcarbodiimide hydrochloride in 30 ml of dichloromethane was stirred at RT overnight. The reaction mixture was washed successively with 1N hydrochloric acid, 1N sodium bicarbonate solution and with water. After drying over sodium sulfate, filtering and concentrating, the residue was chromatographed on silica gel. 2.09 g of the title compound were obtained as a colorless oil.

LC/MS (method C): $R_t$=3.63 min, m/z: 389.17 [M−Boc+H$^{+}$].

B. Benzyl(R)-2-amino-3-(2-benzyloxycarbonylaminoethylsulfanyl)propionate

A solution of 0.50 g (1.023 mmol) of benzyl(R)-3-(2-benzyloxycarbonylaminoethylsulfanyl)-2-tert-butoxycarbonylaminopropionate in 5 ml of dichloromethane was mixed with the same volume of trifluoroacetic acid and left to stand at RT for 1 h. It was then concentrated and directly reacted further.

LC/MS (method A): $R_t$=1.06 min, m/z: 389.1 [MH$^+$].

C. Benzyl(R)-3-(2-benzyloxycarbonylaminoethyl-sulfanyl)-2-[3-(9S,12R)-9-isopropyl-11-oxo-2,7-dioxa-10-azabicyclo[12.2.2]octadeca-[(17), 14(18), 15-trien-12-yl)ureido]propionate A solution of 166 mg (1.02 mmol) of 1,1'-carbonyldiimidazole in 8 ml of DMF was mixed with 515 mg (1.02 mmol) of the trifluoroacetate from step B and 0.57 ml (415 mg, 4.10 mmol) of triethylamine. A solution of 328 mg (1.02 mmol) of (9S,12R)-12-amino-9-isopropyl-2,7-dioxa-10-azabicyclo [12.2.2]octadeca-1(17),14(18),15-trien-11-one (1-1E) in 8 ml of DMF was added to this mixture under argon, and the mixture was stirred at RT overnight. The reaction mixture was then concentrated and separated by preparative HPLC. The required fractions were combined and freed of acetonitrile. The resulting aqueous solution was extracted with ethyl acetate, and the organic phase was dried over sodium sulfate, filtered and concentrated. 222 mg of the title compound were obtained.

LC/MS (method A): $R_t$=1.72 min, m/z: 735.3 [MH$^+$].

D. Benzyl(R)-3-(2-benzyloxycarbonylaminoethane-sulfonyl)-2-[3-(9S,12R)-9-isopropyl-11-oxo-2,7-dioxa-10-azabicyclo[12.2.2]octadeca-1(17),14(18), 15-trien-12-yl)ureido]propionate A mixture of 222 mg (0.30 mmol) of benzyl(R)-3-(2-benzyloxycarbonylaminoethylsulfanyl)-2-[3-((9S,12R)-9-isopropyl-11-oxo-2,7-dioxa-10-azabicyclo[12.2.2]octadeca-1 (17),14(18),15-trien-12-yl)ureido]propionate in 5 ml of methanol and 5 ml of water was cooled to 0 C and 742 mg (1.21 mmol) of Oxone were added in portions. After 2 h, the mixture is diluted with ethyl acetate, and the organic phase is separated off and extracted twice more with ethyl acetate. The combined organic phases were dried over sodium sulfate, filtered and concentrated. 198 mg were obtained and were reacted further without further purification.

LC/MS (method A): $R_t$=1.54 min, m/z: 767.3 [MH$^+$].

E. (R)-3-(2-Aminoethanesulfonyl)-2-[3-((9S,12R)-9-isopropyl-11-oxo-2,7-dioxa-10-azabicyclo[12.2.2] octadeca-1(17),14(18),15-trien-12-yl)ureido]propionic acid 83 mg of 5% palladium/C were added to a solution of 198 mg (0.26 mmol) of benzyl(R)-3-(2-benzyloxycarbonylaminoethanesulfonyl)-2-[3-((9S,12R)-9-isopropyl-11-oxo-2,7-dioxa-10-azabicyclo[12.2.2]octadeca-1(17),14(18),15-trien-12-yl)ureido]propionate in 10 ml of methanol, and the mixture was hydrogenated under a hydrogen atmosphere (balloon pressure). After leaving to stand for 2 days, the mixture was filtered, concentrated and purified by preparative HPLC. The required fractions were combined and freeze dried after addition of 1N hydrochloric acid. 23 mg of the title compound were obtained as hydrochloride.

LC/MS (method C): $R_t$=2.35 min, m/z: 543.26 [MH$^+$].

Example 5-2

(S)-3-(6-Aminopyridin-3-yl)-2-[3-((9S,12R)-9-isopropyl-11-oxo-2,7-dioxa-10-azabicyclo[12.2.2]octadeca-1(17),14(18),15-trien-12-yl)ureido]propionic acid

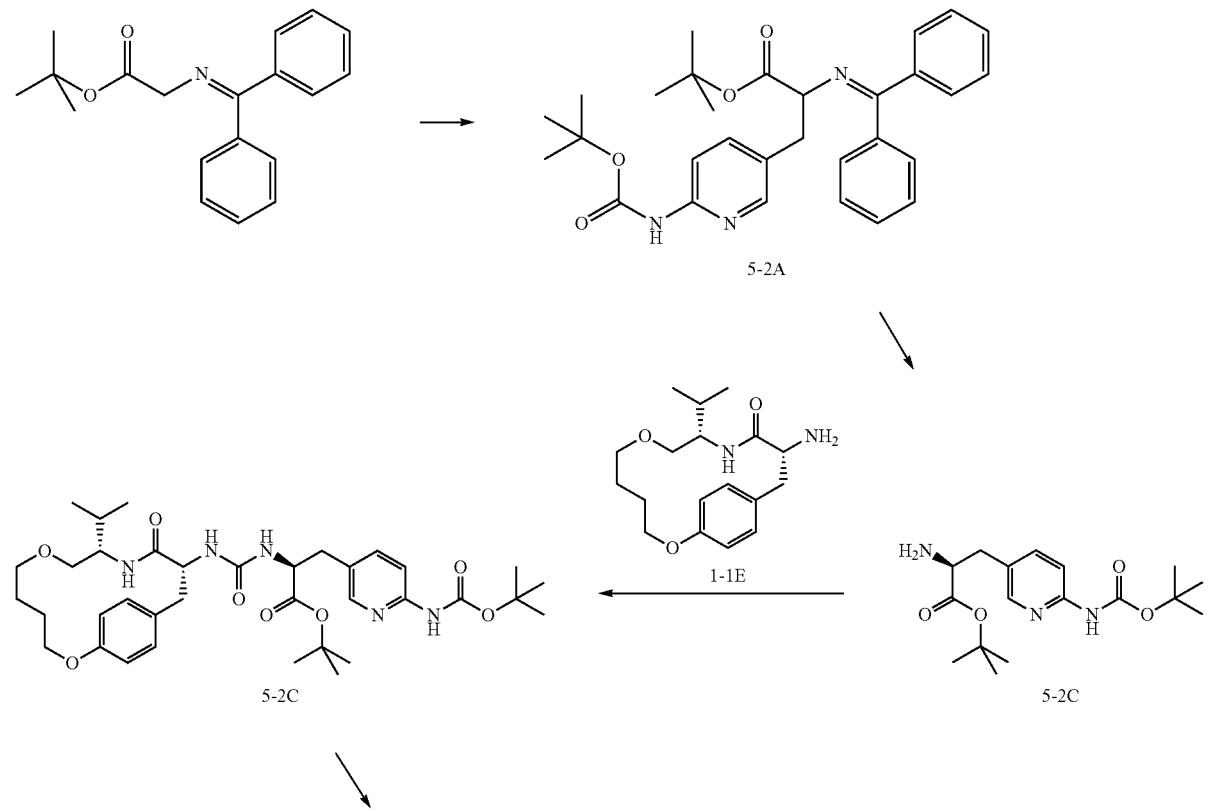

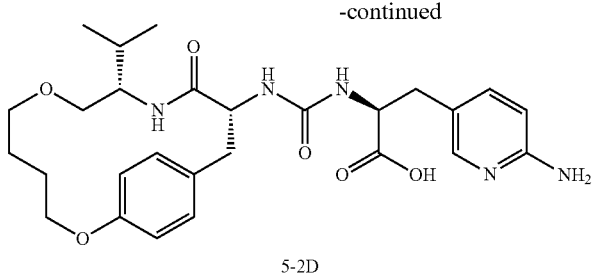

5-2D

A. tert-Butyl 2-(benzhydrylideneamino)-3-(6-tert-butoxycarbonylaminopyridin-3-yl)propionate 84.64 ml (84.64 mmol) of a 1M solution of lithium bis(trimethylsilyl)amide in THF were added dropwise to a solution of 25.00 g (84.64 mmol) of N-(diphenylmethylene)glycine tert-butyl ester in 185 ml of THF under argon at 0° C. After stirring at this temperature for 15 min, 24.31 g (84.64 mmol) of tert-butyl (5-bromomethylpyridin-2-yl)carbamate were added as solid, and stirring was continued for 1 h. The reaction mixture was cautiously diluted with water and extracted with ethyl acetate. The organic phase was dried over sodium sulfate, filtered and concentrated. 44.08 g of the crude product were obtained and were reacted further without further purification.

LC/MS (method A): $R_t$=1.68 min, m/z: 502.2 [MH$^+$].

B. tert-Butyl (S)-2-amino-3-(6-tert-butoxycarbonylaminopyridin-3-yl)propionate After addition of 4.14 g of 10% palladium/carbon to a solution of 19.50 g (38.87 mmol) of the crude product from step A in 1.8 l of methanol it was hydrogenated under autogenous pressure. After the reaction was complete, the mixture was filtered and concentrated. The crude mixture was taken up in heptane and mixed with 45 ml of 1N hydrochloric acid and 90 ml of water, and the aqueous phase was added to 90 ml of 1N sodium hydroxide solution and extracted four times with ethyl acetate. The combined organic phases were dried over sodium sulfate, filtered and concentrated. The racemate was separated by chiral chromatography.

LC/MS (method A): $R_t$=0.89 min, m/z: 338.1 [MH$^+$].
Chiral chromatography (Chiralpak AD-H/44, 250×4.6 mm, ethanol:methanol 1:1+0.1% diethylamine, 40 min): $R_t$=17.48 min.

C. tert-Butyl (S)-3-(6-tert-butoxycarbonylaminopyridin-3-yl)-2-[3-((9S,12R)-9-isopropyl-11-oxo-2,7-dioxa-10-azabicyclo[12.2.2]octadeca-1 (17),14(18),15-trien-12-yl)ureido]propionate 112 mg (0.69 mmol) of 1,1'-carbonyldiimidazole were added to a mixture of 234 mg (0.69 mmol) of tert-butyl (S)-2-amino-3-(6-tert-butoxycarbonylaminopyridin-3-yl)-propionate and 106 µl (77 mg, 0.76 mmol) of triethylamine in 2.5 ml of DMF. The solution was stirred at RT for 1 h, before a solution of 222 mg (0.69 mmol) of (9S,12R)-12-amino-9-isopropyl-2,7-dioxa-10-azabicyclo[12.2.2]octadeca-1(17),14(18),15-trien-11-one (1-1E) in 2.5 ml of DMF was added. The mixture was left to stand overnight and then concentrated and partitioned between water and ethyl acetate. The organic phase was separated off, dried over sodium sulfate, filtered and concentrated. The residue was purified by preparative HPLC. The required fractions were combined, freed of acetonitrile, made slightly alkaline with sodium bicarbonate and extracted with ethyl acetate. The organic phase was dried over sodium sulfate, filtered and concentrated.

LC/MS (method A): $R_t$=1.47 min, m/z: 684.3 [MH$^+$].

D. (S)-3-(6-Aminopyridin-3-yl)-2-[3-((9S,12R)-9-isopropyl-11-oxo-2,7-dioxa-10-azabicyclo[12.2.2] octadeca-1(17),14(18),15-trien-12-yl)ureido]propionic acid 160 mg (0.23 mmol) of tert-butyl (S)-3-(6-tert-butoxycarbonylaminopyridin-3-yl)-2-[3-(9S,12R)-9-isopropyl-11-oxo-2,7-dioxa-10-azabicyclo[12.2.2]octadeca-1(17),14(18),15-trien-12-yl)ureido]propionate were dissolved in 6 ml of dichloromethane and, after addition of the same volume of TFA, stirred at RT. After 5 h, the mixture was concentrated and purified by preparative HPLC. The required fractions were combined, freed of acetonitrile, mixed with 1N hydrochloric acid, concentrated further and finally freeze dried. 108 mg of the title compound were obtained as hydrochloride.

LC/MS (method A): $R_t$=0.92 min, m/z: 528.3 [MH$^+$].

Example 5-3

(S)-3-(6-Aminopyridin-3-yl)-2-[3-((9S,12R)-9-cyclopropyl-11-oxo-2,7-dioxa-10-azabicyclo[12.2.2] octadeca-1(17),14(18),15-trien-12-yl)ureido]propionic acid The title compound was prepared in analogy to Example 5-2 from (S)-2-amino-2-cyclopropylethanol (U.S. Pat. No. 6,191,306) instead of 1-1E using (9S,12R)-12-amino-9-cyclopropyl-2,7-dioxa-10-azabicyclo[12.2.2]octadeca-1(17), 14(18),15-trien-11-one.

LC/MS (method J): $R_t$=2.39 min, m/z: 526.41 [MH$^+$].

Example 5-4

(S)-6-Amino-2-[3-((9S,12R)-9-isopropyl-11-oxo-2, 7-dioxa-10-azabicyclo[12.2.2]octadeca-1(17),14(18), 15-trien-12-yl)ureido]-6-methylheptanoic acid The title compound is obtained in analogy to Example 5-2 by using ethyl (S)-2,6-diamino-6-methylheptanoate hydrochloride with the addition of triethylamine as auxiliary base.

LC/MS (method C): $R_t$=2.34 min, m/z: 521.26 [MH$^+$].

Example 5-5

Ethyl (S)-3-(6-aminopyridin-3-yl)-2-[3-((9S,12R)-9-isopropyl-11-oxo-2,7-dioxa-10-azabicyclo[12.2.2] octadeca-1-(17),14(18), 15-trien-12-yl)ureido]propionate The title compound is obtained in analogy to Example 5-2 by using N-(diphenylmethylene)glycine ethyl ester instead of N-(diphenylmethylene)glycine tert-butyl ester.

LC/MS (method C): $R_t$=2.53 min, m/z: 556.2 [MH$^+$].

The following compound was prepared in an analogous manner:

Example 5-6

(S)-2-[3-((9S,12R)-9-Isopropyl-11-oxo-2,7-dioxa-10-azabicyclo[12.2.2]octadeca-1(17),14(18),15-trien-12-yl)ureido]-3-piperidin-3-ylpropionic acid LC/MS (method I): $R_t$=1.20 min, m/z: 519.38 [MH$^+$].

Example 5-7

(S)-3-(6-Aminopyridin-3-yl)-2-[3-((9S,12R)-9-methyl-11-oxo-2,7-dioxa-10-azabicyclo[12.2.2]octadeca-1(17),14(18),15-trien-12-yl)ureido]propionic acid LC/MS (method B): $R_t$=0.54 min, m/z: 500.3 [MH$^+$].

Example 6-1

(S)-3-(6-Aminopyridin-3-yl)-2-[3-((8S,11R)-8-isopropyl-10-oxo-6-oxa-1,9,14-triazabicyclo[11.2.1]hexadeca-13(16),14-dien-11-yl)ureido]propionic acid

A. (R)-3-(1-Allyl-1H-imidazol-4-yl)-2-benzyloxycarbonylaminopropionic acid 3.53 ml (4.24 g, 24.84 mmol) of benzyl chloroformate were added to a solution of 4.85 g (24.84 mmol) of (R)-3-(1-allyl-1H-imidazol-4-yl)-2-aminopropionic acid (as described for the (S)-enantiomer in Bioorg. Med. Chem. 2006, 14, 5981-5988) in 13 ml of 2N sodium hydroxide solution while stirring at 0° C., and stirring was continued at this temperature with addition of a further 13 ml of 2N sodium hydroxide solution for 2 h, and the mixture was them warmed to RT. The reaction mixture was covered with a layer of ethyl acetate, and the pH was adjusted to 3 to 4 with 6N hydrochloric acid. The organic phase was separated off, and the aqueous phase was washed again with ethyl acetate and then freeze dried. The residue was mixed with THF and DMF until stirrable and was thoroughly stirred, and the suspension was filtered. The resulting solution was concentrated and reacted without further purification in the next step.

LC/MS (method B): $R_t$=0.52 min, m/z: 330.2 [MH$^+$].

B. Benzyl[(R)-2-(1-allyl-1H-imidazol-4-yl)-1-(S)-1-allyloxymethyl-2-methylpropylcarbamoyl)ethyl]carbamate A solution of the material from step A in 180 ml of DMF was mixed with 4.18 g (27.32 mmol) of N-hydroxybenzotriazole and 5.64 g (27.32 mmol) of N,N'-dicyclohexylcarbodiimide and stirred at RT for 2 h. Addition of 3.56 g (24.84 mmol) of (S)-1-allyloxymethyl-2-methylpropylamine (1-1B) was followed by stirring at RT for a further 24 h and then concentration, and the residue was partitioned between ethyl acetate and saturated NaHCO$_3$ solution. The organic phase was dried over Na$_2$SO$_4$, filtered and concentrated. The residue was purified by preparative HPLC. After washing with saturated NaHCO$_3$ solution, 5.02 g of the title compound are obtained.

LC/MS (method B): $R_t$=0.75 min, m/z: 454.9 [MH$^+$].

C. Benzyl ((8S,11R)-8-isopropyl-10-oxo-6-oxa-1,9,14-triazabicyclo[11.2.1]hexadeca-3,13(16),14-trien-11-yl)carbamate A solution of 0.735 g (1.62 mmol) of benzyl[(R)-2-(1-allyl-1H-imidazol-4-yl)-1-(S)-1-allyloxymethyl-2-methylpropylcarbamoyl)ethyl]carbamate in 370 ml of dichloromethane was mixed with 0.210 g (0.24 mmol) of benzylidene[1,3-bis(2,4,6-trimethylphenyl)-2-imidazolidinylidene]dichloro(tricyclohexylphosphine)ruthenium (Grubbs II catalyst) and stirred at RT. The mixture was stirred at RT for several days with repeated addition of Grubbs II catalyst until starting material was no longer present (LC/MS). The mixture was concentrated and the residue was chromatographed on silica gel (dichloromethane/methanol 99:1→9:1). 0.506 g of the title compound was obtained.

LC/MS (method B): $R_t$=0.64 min, m/z: 427.3 [MH$^+$].

D. (8S,11R)-11-Amino-8-isopropyl-6-oxa-1,9,14-triazabicyclo[11.2.1]hexadeca-13(16),14-dien-10-one A solution of 0.49 g (1.14 mmol) of benzyl ((8S,11R)-8-isopropyl-10-oxo-6-oxa-1,9,14-triazabicyclo[11.2.1]hexadeca-3,13(16),14-trien-11-yl)carbamate from step C in 80 ml of methanol was hydrogenated over 0.12 g of palladium on carbon (10%) under a hydrogen atmosphere under autogenous pressure at RT. After the starting material had completely reacted, the mixture was filtered and concentrated. The residue was purified by preparative HPLC. 0.06 g of the title compound was obtained.

LC/MS (method B): $R_t$=0.22 min, m/z: 295 [MH$^+$]

E. tert-Butyl (S)-3-(6-tert-butoxycarbonylaminopyridin-3-yl)-2-[3-((8S,11R)-8-isopropyl-10-oxo-6-oxa-1,9,14-triazabicyclo[11.2.1]hexadeca-13(16),14-dien-11-yl)ureido]propionate A solution of 56 mg (190 µmol) of (8S,11R)-11-amino-8-isopropyl-6-oxa-1,9,14-triazabicyclo[11.2.1]hexadeca-13(16),14-dien-10-one from step D in 5 ml of DMF was cooled to 0° C. and, while stirring, 32 mg (194 µmol) of 1,1'-carbonyldiimidazole were added. The mixture was stirred for 30 min, and then 64 mg (190 µmol) of tert-butyl (S)-2-amino-3-(6-tert-butoxycarbonylaminopyridin-3-yl)propionate were added, and the mixture was warmed to RT. After standing overnight, the same amount of 1,1'-carbonyldiimidazole was again added, and the mixture was stirred for a further 24 h. It was then concentrated and purified by preparative HPLC. 27 mg of the desired compound were obtained.

LC/MS (method B): $R_t$=0.58 min, m/z: 658.9 [MH$^+$].

F. (S)-3-(6-Aminopyridin-3-yl)-2-[3-((8S,11R)-8-isopropyl-10-oxo-6-oxa-1,9,14-triazabicyclo[11.2.1]hexadeca-13(16),14-dien-11-yl)ureido]propionic acid A solution of 27 mg (41 µmol) in 6 ml of TFA/dichloromethane (1:1, v/v) was stirred at RT for 4 h. It was then concentrated and taken up in 1N hydrochloric acid and subsequently freeze dried. 20 mg of the title compound were obtained as hydrochloride.

LC/MS (method B): $R_t$=0.36 min, m/z: 502.9 [MH$^+$].

Example 6-2

(S)-3-(6-Aminopyridin-3-yl)-2-[3-((3R,6S)-6-isopropyl-4-oxo-8-oxa-5-azabicyclo[11.2.2]heptadeca-1(16),13(17),14-trien-3-yl)ureido]propionic acid

A. (R)-3-(4-Allylphenyl)-2-tert-butoxycarbonylaminopropionic acid

A solution of 2.03 g (6.36 mmol) of methyl (R)-3-(4-allylphenyl)-2-tert-butoxycarbonylaminopropionate (prepared as in Synlett, 2005, 12, 1877-1880) in 20 ml of dioxane/water (1:1, v/v) and 0.30 g (12.71 mmol) of lithium hydroxide was stirred at RT for 2 h and then neutralized with 1N hydrochloric acid. The reaction mixture was extracted with ethyl acetate, and the organic phase was dried over $Na_2SO_4$, filtered and concentrated. 1.90 g of the title compound were obtained.

LC/MS (method B): $R_t$=0.97 min, m/z: 206.0 [$MH^+$].

The compound was employed instead of (R)-3-(4-allyloxyphenyl)-2-(9H-fluoren-9-ylmethoxycarbonylamino)propionic acid in order to prepare Example 6-2 in analogy to Example 5-2. The Boc protective group used instead of the Fmoc protective group was eliminated in a known manner with dichloromethane/TFA mixtures.

LC/MS (method I): $R_t$=1.29 min, m/z: 512.3 [$MH^+$].

Example 6-3

(S)-3-(6-Aminopyridin-3-yl)-2-[3-(9S,12R)-16-fluoro-9-isopropyl-11-oxo-2,7-dioxa-10-azabicyclo[12.2.2]octadeca-1(17),14(18),15-trien-12-yl)ureido]propionic acid

A. (R)-3-(4-Allyloxy-3-fluorophenyl)-2-tert-butoxycarbonylaminopropionic acid 1.18 g (60%, 29.39 mmol) of sodium hydride were added to a solution of 4.0 g (13.36 mmol) of (R)-2-tert-butoxycarbonylamino-3-(3-fluoro-4-hydroxyphenyl)propionic acid in 23 ml of DMF while stirring at 0° C., and the mixture was stirred at this temperature. After 15 min, 1.27 ml (1.78 g, 14.7 mmol) of allyl bromide were added, and stirring was continued for 1 h while the mixture reached RT. It was quenched with methanol and, after cooling, excess methanol was removed in a rotary evaporator. Dilution with diethyl ether was followed by acidification with 1N hydrochloric acid, and the aqueous phase was extracted twice more with diethyl ether, and the combined organic phases were washed with saturated sodium chloride solution, dried over $NaSO_4$, filtered and concentrated. 4.50 g of a yellowish oil were obtained.

LC/MS (method B): $R_t$=0.94 min, m/z: 239.9 [$MH^+$].

The compound was employed instead of (R)-3-(4-allyloxyphenyl)-2-(9H-fluoren-9-ylmethoxycarbonylamino)propionic acid in order to prepare Example 6-3 in analogy to Example 5-2. The Boc protective group used instead of the Fmoc protective group was eliminated in a known manner with dichloromethane/TFA mixtures.

LC/MS (method E): $R_t$=2.40 min, m/z: 546.43 [$MH^+$].

The following examples were prepared in the same manner as above using (R)-3-allyloxy-2-tert-butoxycarbonylaminopropionic acid (prepared analogously in JACS, 129 (22), 6986-6987, 2007) instead of (R)-3-(4-allyloxyphenyl)-2-(9H-fluoren-9-ylmethoxycarbonylamino)propionic acid:

| Example | Name | $R_t$ (min) | m/z [$MH^+$] | Method |
|---|---|---|---|---|
| 6-4 | (S)-3-(6-Aminopyridin-3-yl)-2-[3-((3S,6R)-3-isopropyl-5-oxo-1,8-dioxa-4-azacyclododec-6-yl)ureido]propionic acid | 1.42 | 452.29 | G |
| 6-5 | Methyl (S)-3-(6-aminopyridin-3-yl)-2-[3-((3S,6R)-3-isopropyl-5-oxo-1,8-dioxa-4-azacyclododec-6-yl)ureido]propionate | 2.40 | 466.33 | D |
| 6-6 | (S)-6-Amino-2-[3-((3S,6R)-3-isopropyl-5-oxo-1,8-dioxa-4-azacyclododec-6-yl)ureido]-hexanoic acid | 1.94 | 417.23 | C |

Example 6-7

(S)-6-Amino-2-[3-((9S,12S)-9-isopropyl-11-oxo-2,7-dioxa-10-azabicyclo-[12.2.2]octadec-12-yl)ureido]hexanoic acid

A. (S)-2-tert-Butoxycarbonylamino-3-(4-hydroxycyclohexyl)propionic acid 0.74 g (7.17 mmol) of rhodium was added to a solution of 7.00 g (24.88 mmol) of (S)-2-tert-butoxycarbonylamino-3-(4-hydroxyphenyl)propionic acid in 50 ml of methanol, and hydrogenation was carried out at 50 C/6 bar pressure of hydrogen. After conversion was complete, the catalyst was filtered off and the filtrate was concentrated. The product was pure enough for further reactions.

LC/MS (method K): $R_t$=1.00 min, m/z: 188.2 [$MH^+$].

B. (S)-3-(4-Allyloxycyclohexyl)-2-tert-butoxycarbonylaminopropionic acid

C. solution of 5.42 g (18.86 mmol) of (S)-2-tert-butoxycarbonylamino-3-(4-hydroxy-cyclohexyl) propionic acid in 20 ml of DMF was added dropwise over the course of 30 min to a suspension of 1.89 g (47.14 mmol) of 60% sodium hydride in 20 ml of DMF at 0° C.

Then 2.28 g (18.86 mmol) of allyl bromide were added, and the mixture was warmed to RT and then stirred for 3 h. It was cautiously quenched with water and concentrated. The residue was dissolved in water and washed with ethyl acetate. The aqueous phase was adjusted to pH 2 with 6M HCl and extracted with ethyl acetate. The organic phase was dried over $Na_2SO_4$, filtered and concentrated. The title compound obtained in this way was reacted further without further purification.

LC/MS (method K): $R_t$=1.46 min, m/z: 228.1 [$MH^+$-Boc].

The further reactions to give Example 6-7 were carried out as described above by employing B. instead of D-Boc-O-allyltyrosine.

LC/MS (method F): $R_t$=2.8 min, m/z: 499.55 [$MH^+$].

Example 7-1

(S)-6-Amino-2-[3-((8S,11R)-8-isopropyl-3,10-di-oxo-6-oxa-2,9-diazabicyclo[11.2.2]heptadeca-1(16),13(17),14-trien-11-yl)ureido]hexanoic acid

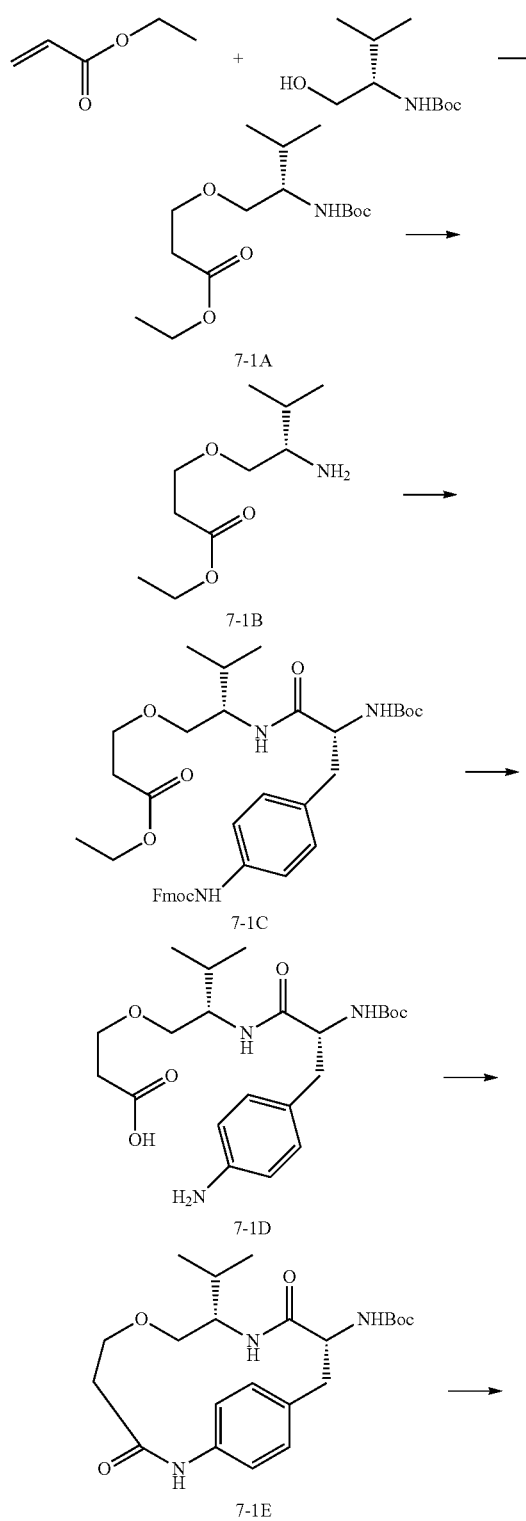

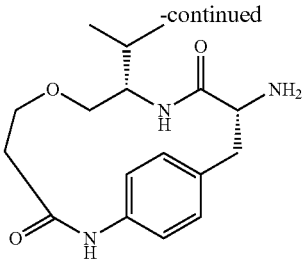

A. Ethyl 3-((S)-2-tert-butoxycarbonylamino-3-methylbutoxy)propionate

About 200 mg of sodium were added to a solution of 3.00 g (14.76 mmol) of Boc-L-valinol in 20 ml of absol. THF under argon. After 2 h, the solution was transferred by needle into an argon-flushed flask—leaving undissolved sodium behind. 2.25 ml (2.22 g, 22.14 mmol) of ethyl acrylate were added to the solution, and the mixture was stirred at room temp. for 2 h. 6 drops of glacial acetic acid were added to the reaction mixture, which was concentrated under reduced pressure. The residue obtained in this way (4.45 g of colorless oil) was employed crude in the next stage.

B. Ethyl 3-((S)-2-amino-3-methylbutoxy)propionate

The crude product (~4.45 g) obtained in 7-1 A was dissolved in a mixture of 10 ml of $CH_2Cl_2$ and 10 ml of TFA and stirred at room temp. for 2 h. After the reaction was complete, the mixture was concentrated in vacuo and codistilled with toluene several times. The crude product obtained in this way was purified by preparative HPLC (acetonitrile/water+addition of 0.5% TFA). 370 mg of ethyl 3-((S)-2-amino-3-methylbutoxy)propionate were obtained in this way as trifluoroacetate in the form of a colorless oil (yield ~8%).

LC/MS (method B): $R_t$=0.52 min, m/z: 204.3 [MH$^+$].

C. Ethyl 3-((S)-2-{(R)-2-tert-butoxycarbonylamino-3-[4-(9H-fluoren-9-ylmethoxy-carbonylamino)phenyl]propionylamino}-3-methylbutoxy)propionate 158.7 mg (1.17 mmol) of HOAt, 0.6 ml (3.5 mmol) of N,N-diisopropylethylamine and 443.3 mg (1.17 mmol) of HATU were successively added to a mixture of 586.0 mg (1.17 mmol) of R)-2-tert-butoxycarbonylamino-3-[4-(9H-fluoren-9-ylmethoxycarbonylamino)phenyl]propionic acid and 370.0 mg (1.17 mmol) of ethyl 3-((S)-2-amino-3-methylbutoxy)propionate in 10 ml of DMF, and the mixture was stirred at room temp. for 2 h. The reaction mixture was concentrated in vacuo. The remaining residue was taken up in dichloromethane, washed with sat. NaHCO$_3$ solution, dried and freed of solvent under reduced pressure. The crude product obtained in this way was purified by flash chromatography on silica gel (heptane/ethyl acetate 1:1). 355.0 mg of pure ethyl 3-((S)-2-{(R)-2-tert-butoxycarbonylamino-3-[4-(9H-fluoren-9-ylmethoxy-carbonylamino)phenyl]propionylamino}-3-methylbutoxy)propionate are obtained in this way (yield ~44%).

LC/MS (method B): $R_t$=1.23 min, m/z: 588.3 [M−Boc+H$^+$].

D. 3-{(S)-2-[(R)-3-(4-Aminophenyl)-2-tert-butoxycarbonylaminopropionylamino]-3-methylbutoxy}propionic acid 355.0 mg (0.52 mmol) of ethyl 3-((S)-2-{(R)-2-tert-butoxycarbonylamino-3-[4-(9H-fluoren-9-ylmethoxycarbonylamino)phenyl]propionylamino}-3-methylbutoxy)propionate were dissolved in a mixture of 9 ml of THF and 3 ml of MeOH. 1.29 ml (1.29 mmol) of an aqueous 1M LiOH solution were added, and the resulting reaction mixture was stirred at room temp. for 1 h. After the reaction was complete, the mixture was neutralized by adding a little aqueous 1N HCl solution, concentrated under reduced pressure and codistilled with toluene. The product obtained in this way (225.0 mg) was employed crude in the next reaction.

LC/MS (method B): $R_t$=0.63 min, m/z: 438.3 [MH$^+$].

E. tert-Butyl ((8S,11R)-8-isopropyl-3,10-dioxo-6-oxa-2,9-diazabicyclo[11.2.2]heptadeca-1(16),13(17),14-trien-11-yl)carbamate The 3-{(S)-2-[(R)-3-(4-aminophenyl)-2-tert-butoxycarbonylaminopropionylamino]-3-methylbutoxy}propionic acid (~225 mg) obtained as crude product in 7-1 D was dissolved in 225 ml of DMF. 70.0 mg (0.51 mmol) of HOAt, 0.26 ml (1.5 mmol) of N,N-diisopropylethylamine and 195.4 mg (0.51 mmol) of HATU were successively added to this solution, and the mixture was stirred at room temp. for 1 h. The reaction mixture was concentrated in vacuo. The residue obtained in this way was taken up in CH$_2$Cl$_2$, washed with sat. NaHCO$_3$ solution, dried over MgSO$_4$ and freed of solvent in vacuo. The ring-closed compound obtained in this way was employed crude in the next stage. Yield: 215.0 mg.

LC/MS (method B): $R_t$=0.76 min, m/z: 364.3 [M−tBu+H$^+$].

F. (8S,11R)-11-Amino-8-isopropyl-6-oxa-2,9-diazabicyclo[11.2.2]heptadeca-1(16),13(17),14-triene-3,10-dione The crude product (~215 mg) obtained in 7-1 E was stirred in a mixture of 4.75 ml of TFA, 0.13 ml of water and 0.13 ml of triisopropylsilane at room temp. for 2 h. After the reaction was complete, the mixture was concentrated in vacuo and codistilled with toluene several times. The crude product obtained in this way was purified by preparative HPLC (acetonitrile/water+addition of 0.1% TFA). 80 mg of (8S,11R)-11-amino-8-isopropyl-6-oxa-2,9-diazabicyclo[11.2.2]hepta-deca-1(16),13(17),14-triene-3,10-dione were obtained in this way as trifluoroacetate in the form of a colorless amorphous material.

LC/MS (method B): $R_t$=0.44 min, m/z: 321.3 [MH$^+$].

G. tert-Butyl (S)-6-tert-butoxycarbonylamino-2[3-((8S,11R)-8-isopropyl-3,10-dioxo-6-oxa-2,9-diazabicyclo[11.2.2]heptadeca-1(16),13(17),14-trien-11-yl)ureido]hexanoate 81.9 mg (0.41 mmol) of 4-nitrophenyl chloroformate were dissolved in 3 ml of CH$_2$Cl$_2$. While cooling in an ice bath, a solution of 80 mg (0.19 mmol) of the (8S,11R)-11-amino-8-isopropyl-6-oxa-2,9-diazabicyclo[11.2.2]heptadeca-1(16),13(17),14-triene-3,10-dione obtained in 7-1 F and 69 μl (0.41 mmol) of N,N-diisopropylethylamine in 3 ml of CH$_2$Cl$_2$ were added. The mixture was then stirred at room temp. for 3 h. The reaction mixture was washed with sat. NaHCO$_3$ solution, water and saturated NaCl solution, dried over MgSO$_4$ and concentrated in vacuo. The residue obtained in this way was dissolved in 3 ml of DMF and mixed with a solution of 68.8 mg (0.2 mmol) of H-Lys(Boc)-OtBu hydrochloride and 65.9 μl (0.39 mmol) of N,N-diisopropylethylamine in 3 ml of DMF. The reaction mixture was stirred at room temp. overnight and then concentrated in vacuo. The crude product obtained in this way was purified by flash chromatography on silica gel (heptane/ethyl acetate 1:1). Yield: 20 mg of tert-butyl (S)-6-tert-butoxycarbonylamino-2-[3-((8S,11R)-8-isopropyl-3,10-dioxo-6-oxa-2,9-diazabicyclo[11.2.2]heptadeca-1(16),13(17),14-trien-11-yl)ureido]hexanoate.

LC/MS (method B): $R_t$=0.91 min, m/z: 648.5 [MH$^+$].

H. (S)-6-Amino-2-[3-((8S,11R)-8-isopropyl-3,10-dioxo-6-oxa-2,9-diazabicyclo[11.2.2]heptadeca-1(16),13(17),14-trien-11yl)ureido]hexanoic acid 20.0 mg (0.03 mmol) of tert-butyl (S)-6-tert-butoxycarbonylamino-2-[3-((8S,11R)-8-isopropyl-3,10-dioxo-6-oxa-2,9-diazabicyclo[11.2.2]heptadeca-1(16),13(17),14-trien-11-yl)ureido]hexanoate were stirred in a mixture of 0.95 ml of TFA, 25 μl of water and 25 μl of triisopropylsilane at room temp. for 2 h. After the reaction was complete, the mixture was concentrated in vacuo and codistilled with toluene several times. The crude product obtained in this way was purified by preparative HPLC (acetonitrile/water+addition of 0.1% TFA). 5 mg of the title compound were obtained in this way as trifluoroacetate in the form of a colorless amorphous material.

LC/MS (method B): $R_t$=0.47 min, m/z: 492.3 [MH$^+$].

The following examples were prepared in an analogous manner:

Example 7-2

(S)-3-(6-Aminopyridin-3-yl)-2-[3-((8S,11R)-8-methyl-3,10-dioxo-6-oxa-2,9-diazabicyclo[11.2.2]heptadeca-1(16),13(17),14-trien-11yl)ureido]propionic acid LC/MS (method B): $R_t$=0.28 min, m/z: 499.25 [MH$^+$].

Example 7-3

(S)-3-(6-Aminopyridin-3-yl)-2-[3-((3S,6R)-3-isopropyl-5,9-dioxo-1-oxa-4,10-diazacyclotridec-6-yl)ureido]propionic acid LC/MS (method B): $R_t$=0.42 min, m/z: 479.33 [MH$^+$].

Example 7-4

(S)-3-(6-Aminopyridin-3-yl)-2-[3-((8S,11R)-8-isopropyl-2,10-dioxo-6-oxa-3,9-diazabicyclo[11.2.2]heptadeca-1(16),13(17),14-trien-11-yl)ureido]propionic acid LC/MS (method A): $R_t$=0.82 min, m/z: 527.20 [MH$^+$].

Example 8-1

(S)-6-Amino-2-[3-(9S,12R)-4,5-dihydroxy-9-isopropyl-11-oxo-2,7-dioxa-10-azabicyclo[12.2.2]octadeca-1(17), 14(18), 15-trien-12-yl)ureido]hexanoic acid A. (9S,12R)-12-Amino-9-isopropyl-2,7-dioxa-10-azabicyclo[12.2.2]octadeca-1(17),4,14(18),15-tetraen-11-one A solution of 3.66 g (6.78 mmol) of 9H-fluoren-9-yl methyl ((9S,12R)-9-isopropyl-11-oxo-2,7-dioxa-10-azabicyclo[12.2.2]octadeca-1(17),4,14(18),15-tetraen-12-yl)carbamate (1-1D) in 300 ml of dichloromethane was mixed with 75 ml of diethylamine and stirred at RT for 5 h. The mixture was concentrated and purified by preparative HPLC. Acetonitrile was removed from the combined product fractions in a rotary evaporator, saturated NaHCO$_3$ solution was added, and the mixture was extracted twice with ethyl acetate, saturated with sodium chloride and again extracted with ethyl acetate.

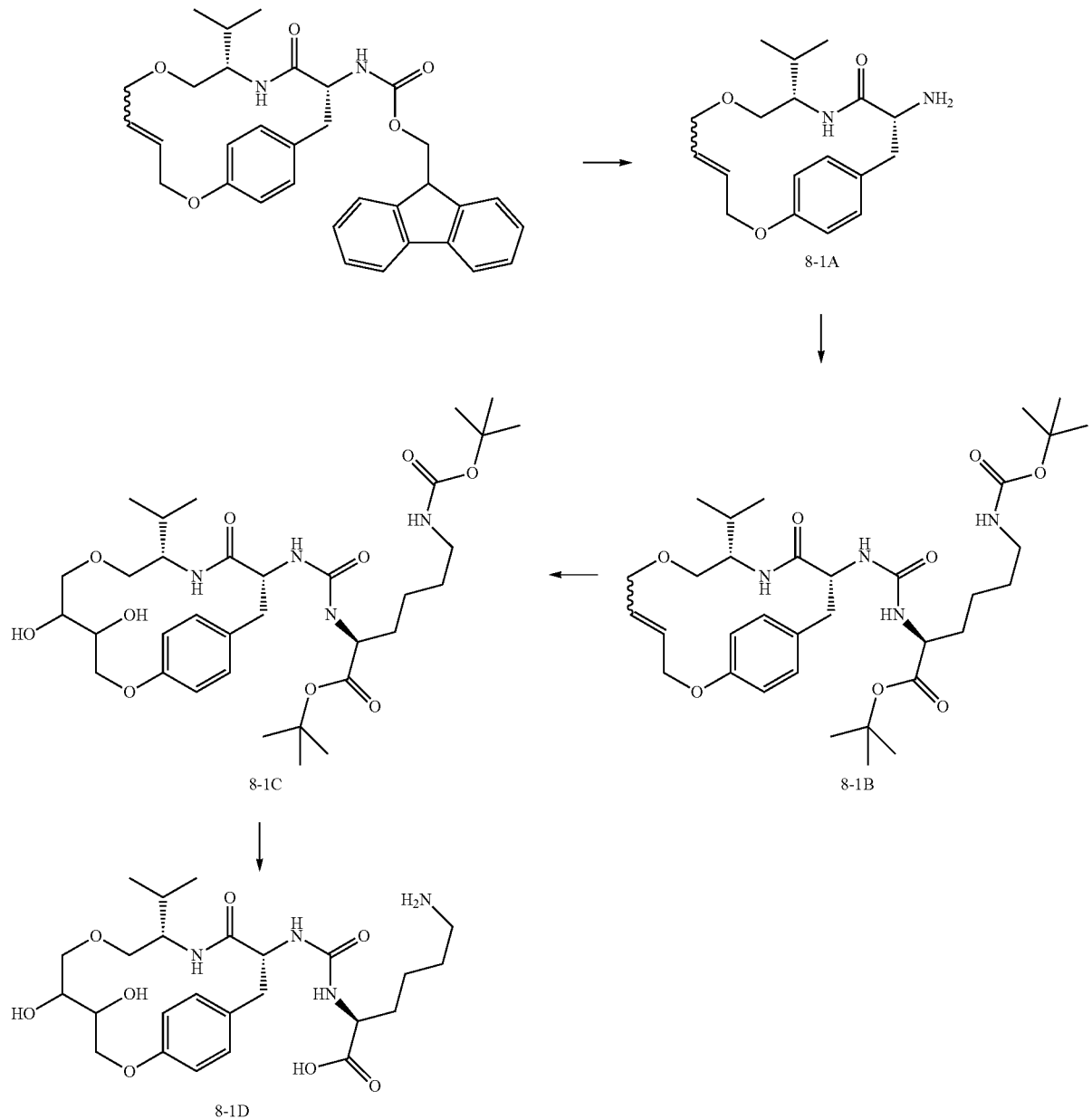 [SMILES: CC(C)[C@H]1COCC=CCOc2ccc(cc2)C[C@@H](NC(=O)OCC2c3ccccc3-c3ccccc32)C(=O)N1 ; CC(C)[C@H]1COCC=CCOc2ccc(cc2)C[C@@H](N)C(=O)N1 ; CC(C)[C@H]1COCC(O)C(O)COc2ccc(cc2)C[C@@H](NC(=O)N[C@@H](CCCCNC(=O)OC(C)(C)C)C(=O)OC(C)(C)C)C(=O)N1 ; CC(C)[C@H]1COCC=CCOc2ccc(cc2)C[C@@H](NC(=O)N[C@@H](CCCCNC(=O)OC(C)(C)C)C(=O)OC(C)(C)C)C(=O)N1 ; CC(C)[C@H]1COCC(O)C(O)COc2ccc(cc2)C[C@@H](NC(=O)N[C@@H](CCCCN)C(=O)O)C(=O)N1]

The combined ethyl acetate phases were dried over Na$_2$SO$_4$, filtered and concentrated. The resulting substance was pure enough for further reactions.

LC/MS (method B): R$_t$=0.58 min, m/z: 319.2 [MH$^+$].

B. tert-Butyl (S)-6-tert-butoxycarbonylamino-2-[3-(9S,12R)-9-isopropyl-11-oxo-2,7-dioxa-10-azabicyclo[12.2.2]octadeca-1(17),4,14(18), 15-tetraen-12-yl)ureido]hexanoate The reaction took place as described in 1-1 F. 1.13 g of the title compound were obtained.

LC/MS (method B): R$_t$=1.00 min, m/z: 647.3 [MH$^+$].

C. tert-Butyl (S)-6-tert-butoxycarbonylamino-2-[3-((9S,12R)-4,5-dihydroxy-9-isopropyl-11-oxo-2,7-dioxa-10-azabicyclo[12.2.2]octadeca-1 (17),14(18), 15-trien-12-yl)ureido]hexanoate 8 mg (9.7 μmol) of (DHQ)2PHAL (hydroquinine 1,4-phthalazinediyl diether) were added to a mixture of 541 mg (387 mmol) of AD-Mix-alpha and 3 mg (7.7 μmol) of potassium osmate in tert-butanol/water (1:1, v/v). After a clear solution had formed, the reaction mixture was cooled to 0° C., 41 mg (425 μmol) of methanesulfonamide were added, and the mixture was stirred at this temperature for 15 min. Then 250 mg (387 μmol) of tert-butyl (S)-6-tert-butoxycarbonylamino-2-[3-((9S,12R)-9-isopropyl-11-oxo-2,7-dioxa-10-azabicyclo [12.2.2]octadeca-1(17),4,14(18),15-tetraen-12-yl)ureido] hexanoate (step B) were added, and the mixture was warmed to RT and left to stand over the weekend. 195 mg (1.55 mmol) of sodium sulfite were then added, and the mixture was stirred at RT for 1 h. The reaction mixture was extracted with ethyl acetate, and the organic phase was dried over Na$_2$SO$_4$, filtered and concentrated in a rotary evaporator. The residue was purified by preparative HPLC. 164 mg of the title compound were obtained.

LC/MS (method B): R$_t$=0.84 min, m/z: 681.3 [MH$^+$].

D. (S)-6-Amino-2-[3-((9S,12R)-4,5-dihydroxy-9-isopropyl-11-oxo-2,7-dioxa-10-azabicyclo[12.2.2] octadeca-1(17),14(18),15-trien-12-yl)ureido]hexanoic acid The protective groups were eliminated as described above in a TFA/dichloromethane mixture. A mixture of the diastereomers was obtained.

LC/MS (method B): R$_t$=0.42 min (double peak), m/z: 525.3 [MH$^+$].

Example 8-2

(S)-6-Amino-2-[3-((9S,12R)-5-hydroxy-9-isopropyl-11-oxo-2,7-dioxa-10-azabicyclo[12.2.2]octadeca-1 (17),14(18),15-trien-12-yl)ureido]hexanoic acid and (S)-6-amino-2-[3-((9S,12R)-4-hydroxy-9-isopropyl-11-oxo-2,7-dioxa-10-azabicyclo[12.2.2]octadeca-1 (17),14(18),15-trien-12-yl)ureido]hexanoic acid A. tert-Butyl (S)-6-tert-butoxycarbonylamino-2-[3-((9S,12R)-5-hydroxy-9-isopropyl-11-oxo-2,7-dioxa-10-azabicyclo[12.2.2]octadeca-1(17),14(18),15-trien-12-yl)ureido]-hexanoate 1.55 ml (773 μmol) (0.5M in THF) of 9-borabicyclo[3.3.1] nonane were added to a solution of 50 mg (77 μmol) of tert-butyl (S)-6-tert-butoxycarbonylamino-2-[3-((9S,12R)-9-isopropyl-11-oxo-2,7-dioxa-10-azabicyclo[12.2.2]octadeca-1(17),4,14(18),15-tetraen-12-yl)ureido]hexanoate (8-1B) in 1.5 ml of THF, and the mixture was stirred at RT overnight. Addition of 250 μl (1.49 mmol) of 6N sodium hydroxide solution and 207 μl (1.83 mmol) of hydrogen peroxide was followed by extraction with dichloromethane. The organic phase was washed with saturated sodium chloride solution, dried over Na$_2$SO$_4$, filtered and concentrated. The residue was purified by preparative HPLC.

LC/MS (method B): R$_t$=0.86 min, m/z: 665.5 [MH$^+$].

B. (S)-6-Amino-2-[3-((9S,12R)-5-hydroxy-9-isopropyl-11-oxo-2,7-dioxa-10-azabicyclo[12.2.2]octadeca-1(17),14 (18),15-trien-12-yl)ureido]hexanoic acid and (S)-6-amino-2-[3-((9S,12R)-4-hydroxy-9-isopropyl-11-oxo-2,7-dioxa-10-azabicyclo[12.2.2]octadeca-1(17),14(18),15-trien-12-yl) ureido]hexanoic acid The protective groups were eliminated as described above in a TFA/dichloromethane mixture and subsequent stirring in 1N HCl.

LC/MS (method B): R$_t$=0.48 min, m/z: 509.2 [MH$^+$].

Example 8-3

3-(6-Aminopyridin-3-yl)-2-[3-((9S,12R)-4,5-dihydroxy-9-isopropyl-11-oxo-2,7-dioxa-10-azabicyclo [12.2.2]octadeca-1(17),14(18),15-trien-12-yl)ureido] propionic acid The title compound was obtained in analogy to the preceding examples.

LC/MS (method L): R$_t$=2.15 min, m/z: 560.26 [MH$^+$].

Example 9-1

(S)-6-Amino-2-[((9S,12R)-9-isopropyl-11-oxo-2,7-dioxa-10-azabicyclo[12.2.2]octadeca-1(17),14(18), 15-trien-12-ylsulfamoyl)amino]hexanoic acid A. tert-Butyl (S)-6-tert-butoxycarbonylamino-2-[((9S,12R)-9-isopropyl-11-oxo-2,7-dioxa-10-azabicyclo[12.2.2]octadeca-1(17),14(18),15-trien-12-ylsulfamoyl)amino]hexanoate A solution of 387 mg (0.858 mmol) of tert-butyl (S)-6-tert-butoxycarbonylamino-2-(2-oxooxazolidine-3-sulfonylamino)hexanoate and 250 mg (0.780 mmol) of (9S,12R)-12-amino-9-isopropyl-2,7-dioxa-10-azabicyclo[12.2.2] octadeca-1(17),14(18),15-trien-11-one (compound 1-1E) in 15 ml of acetonitrile was stirred at 80° C. After 1 day (d), the same amount of the oxazolidine was again added, and the mixture was stirred for 1 d. The reaction mixture was then concentrated and the residue was purified by prep. HPLC. Product-containing fractions were combined, the acetonitrile was evaporated off, made slightly alkaline with sat. NaHCO$_3$ solution and extracted several times with ethyl acetate. The combined organic phases were dried over Na$_2$SO$_4$, filtered and concentrated. 78 mg of the title compound were obtained.

LC/MS (method B): R$_t$=1.16 min, m/z: 585.9 [MH-Boc$^+$].

B. (S)-6-Amino-2-[((9S,12R)-9-isopropyl-11-oxo-2, 7-dioxa-10-azabicyclo[12.2.2]octadeca-1(17),14(18), 15-trien-12-ylsulfamoyl)amino]hexanoic acid A solution of 78 mg (0.114 mmol) of tert-butyl (S)-6-tert-butoxycarbonylamino-2-[((9S,12R)-9-isopropyl-11-oxo-2, 7-dioxa-10-azabicyclo[12.2.2]octadeca-1(17),14(18),15-trien-12-ylsulfamoyl)amino]hexanoate in 3 ml of dichloromethane/TFA (1:1, v/v) was left to stand at RT for 2 h and then concentrated. The crude product was purified by prep. HPLC. The required fractions were combined and freeze dried after addition of 1N hydrochloric acid. 34 mg of the title compound were obtained as hydrochloride. LC/MS (method F): $R_t$=2.97 min, m/z: 529.23 [MH$^+$].

Example 9-2

(S)-6-Amino-2-[((9S,12S)-9-isopropyl-11-oxo-2,7-dioxa-10-azabicyclo[12.2.2]octadeca-1(17), 14(18), 15-trien-12-ylsulfamoyl)amino]hexanoic acid The title compound was obtained in analogy to the preceding examples. LC/MS (method F): $R_t$=2.81 min, m/z: 529.23 [MH$^+$]

Pharmacological Examples

The prepared substances were tested for TAFIa inhibition using the Actichrome plasma TAFI Activity Kit from American Diagnostica (Pr. No. 874). This entailed adding 28 µl of assay buffer (20 mM Hepes, 150 mM NaCl, pH 7.4) and 10 µl of TAFIa (American Diagnostica Pr. No. 874TAFIA; 2.5 µg/ml) to 2 µl of 2.5 mM DMSO solution of the substance and incubating in a 96 half-well microtiter plate at room temperature for 15 minutes. The enzyme reaction was started by adding 10 µl of TAFIa developer (prediluted 1:2 with assay buffer). The time course of the reaction was followed at 420 nm in a microtiter plate reader (SpectraMax plus 384; Molecular Devices) for 15 minutes.

The $IC_{50}$ values were calculated from the averaged values (duplicate determination) of serial dilutions of the substance with the aid of the Softmax Pro software (version 4.8; Molecular Devices).

Table 1 shows the results.

TABLE 1

| Example No. | $IC_{50}$ [µM] |
|---|---|
| 1-1 | 0.006 |
| 1-2 | 9.044 |
| 1-3 | 0.269 |
| 1-4 | 0.071 |
| 1-5 | 0.105 |
| 1-6 | 0.811 |
| 1-7 | 0.049 |
| 1-8 | 0.029 |
| 1-9 | 0.019 |
| 2-1 | 0.0088 |
| 3-1 | 0.0077 |
| 4-1 | 0.017 |
| 5-1 | 0.649 |
| 5-2 | 0.009 |
| 5-3 | 0.032 |
| 6-1 | 0.052 |
| 6-2 | 0.021 |
| 6-3 | 0.012 |
| 6-4 | 0.055 |
| 6-6 | 0.053 |
| 7-1 | 0.022 |
| 7-4 | 0.040 |
| 8-1 | 0.023 |
| 8-2 | 0.033 |
| 8-3 | 0.059 |

The invention claimed is:

1. A compound of the formula I

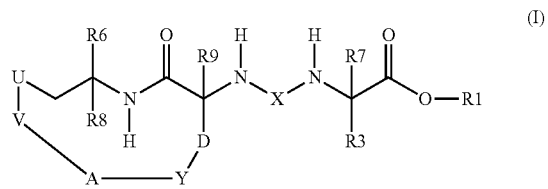

or a stereoisomer of the compound of the formula I and mixtures of these forms in any ratio, where X is —C(O)— or —SO$_2$—, U is oxygen atom, A is —C(O)—NH— or —NH—C(O)—, V is —(C$_2$-C$_9$)-alkylene-, where alkylene is unsubstituted or substituted independently of one another once, twice or three times by —OH, NH$_2$ or halogen, D is —(C$_1$-C$_2$)-alkylene-, Y is phenyl, where phenyl is unsubstituted or substituted independently of one another once, twice or three times by R15, R1 is 1) hydrogen atom, 2) —(C$_1$-C$_6$)-alkyl, 3) —(C$_1$-C$_6$)-alkyl-OH, 4) —(C$_0$-C$_4$)-alkyl-(C$_3$-C$_6$)-cycloalkyl, 5) —(C$_1$-C$_{10}$)-alkyl-O—C(O)—O—R2, 6) —(CH$_2$)$_r$—(C$_6$-C$_{14}$)-aryl, in which aryl is unsubstituted or substituted independently of one another once, twice or three times by R15, and r is the integer zero, 1, 2 or 3, or 7) —(CH$_2$)$_s$-Het, where Het means a 4- to 15-membered heterocyclic ring system having 4 to 15 ring atoms which are present in one, two or three ring systems which are connected together, and which comprise, depending on the ring size, one, two, three or four identical or different heteroatoms from the series oxygen, nitrogen or sulfur, and in which Het is unsubstituted or substituted independently of one another once, twice or three times by R15, and s is the integer zero, 1, 2 or 3, R2 is 1) —(C$_1$-C$_6$)-alkyl, 2) —(CH$_2$)$_r$—(C$_6$-C$_{14}$)-aryl, in which aryl is unsubstituted or substituted independently of one another once, twice or three times by R15, and r is the integer zero, 1, 2 or 3, or 3) —(C$_0$-C$_4$)-alkyl-(C$_3$-C$_6$)-cycloalkyl, R3 is 1) —(C$_2$-C$_6$)-alkylene-NH$_2$, where alkylene is unsubstituted or substituted once, twice, three or four times by halogen, 2) —(C$_1$-C$_4$)-alkylene-O—(C$_1$-C$_4$)-alkylene-NH$_2$, 3) —(C$_1$-C$_4$)-alkylene-SO$_2$—(C$_1$-C$_4$)-alkylene-NH$_2$, 4) —(C$_0$-C$_4$)-alkylene-Het, where Het is as defined above and is substituted by —NH$_2$ and once, twice or three times by R15, 5) —(C$_0$-C$_4$)-alkylene-(C$_3$-C$_8$)-cycloalkyl-NH$_2$ or 6) —(C$_0$-C6)-alkylene-cyclic amine , wherein the cyclic amine is selected from the group consisting of azetidinyl, pyrrolidinyl, piperidinyl, piperazinyl, azepinyl, morpholinyl and thiomorpholinyl,

51

R6 is
1) hydrogen atom,
2) —$(C_1-C_6)$-alkyl, where alkyl is unsubstituted or substituted independently of one another once, twice or three times by R16,
3) —O—$(C_1-C_6)$-alkyl, where alkyl is unsubstituted or substituted independently of one another once, twice or three times by R16,
4) —$(C_0-C_4)$-alkylene-Het, where Het is as defined above, where alkylene and Het are unsubstituted or substituted independently of one another once, twice or three times by R16,
5) —$(C_0-C_4)$-alkylene-aryl, where alkylene and aryl are unsubstituted or substituted independently of one another once, twice or three times by R16, or
6) —$(C_0-C_4)$-alkylene-$(C_3-C_8)$-cycloalkyl, where alkylene and cycloalkyl are unsubstituted or substituted independently of one another once, twice or three times by R16, R7 is hydrogen atom, halogen or —$(C_1-C_6)$-alkyl,
R8 is hydrogen atom, halogen or —$(C_1-C_6)$-alkyl,
R9 is hydrogen atom, halogen or —$(C_1-C_6)$-alkyl,
R15 is hydrogen atom, —$(C_1-C_4)$-alkyl, —O—$CF_3$, —$NH_2$, —OH, —$CF_3$ or halogen, and
R16 is —O—$CF_3$, —$NH_2$, —OH, —$CF_3$ or halogen; or a physiologically tolerated salt thereof.

2. A compound of the formula I as claimed in claim 1, where
A is —C(O)—NH—,
V is
—$(C_2-C_9)$-alkylene-, wherein the alkylene is unsubstituted
or a physiologically tolerated salt thereof.

3. A compound of the formula I according to claim 1 selected from the group consisting of
(S)-6-amino-2((8S,11R)-8-isopropyl-3,10-dioxo-6-oxa-2,9-diazabicyclo[11.2.2]heptadeca-1(16),13(17),14-trien-11-ylamino)hexanoic acid,
(S)-3-(6-aminopyridin-3-yl)-2-((8S,11R)-8-methyl-3,10-dioxo-6-oxa-2,9diazabicyclo [11.2.2]heptadeca-1(16),13(17),14-trien-11-yl)ureido]propionic acid,
(S)-3-(6-aminopyridin-3-yl)-2-[3-((8S,11R)-8-isopropyl-2,10-dioxo-6-oxa-3,9diazabicyclo[11.2.2]heptadeca-1(16),13(17),14-trien-11-yl)ureido]propionic acid, and
(S)-6-Amino-2-[3-((8S,11R)-8-isopropyl-3,10-dioxo-6-oxa-2,9diazabicyclo[11.2.2]heptadeca-1(16),13(17),14-trien-11-yl)ureido]hexanoic acid, or
a physiologically tolerated salt thereof.

4. A process for preparing the compound of the formula I as claimed in claim 1, which comprises
a) reacting a compound of the formula (II)

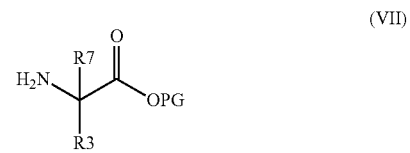

where U, R6 and R8 have the meanings mentioned in the compound of the formula (I), with an amino acid of the formula (III)

52

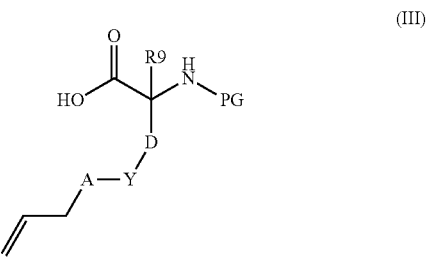

in which R9, A, Y and D have the meanings mentioned in the compound of the formula (I), resulting in a compound of the formula (IV)

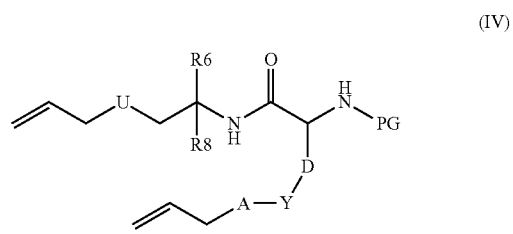

and converting under conditions of ring-closure metathesis and subsequent hydrogenation of the resulting double bond, the compound of the formula (IV) into a compound of the formula (V)

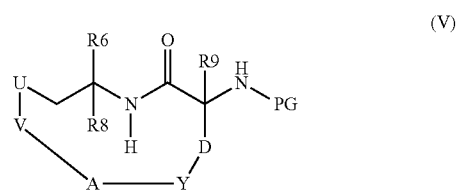

where V is —$(C_2-C_9)$-alkylene-, and subsequently eliminating the protective group PG, and obtaining the compound of the formula (VI),

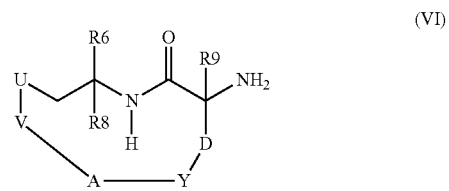

and reacting the compound of the formula (IV) with a compound of the formula (VII)

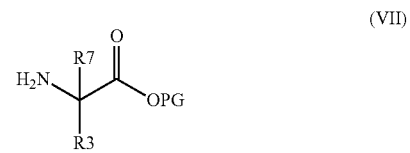

in which R3 and R7 have the meanings mentioned in formula (I), PG is a suitable ester protective group radical, and the nitrogen in R3 is protected where appropriate by a suitable amino protective group, with phosgene or a phosgene equivalent to give a compound of the formula (VIII)

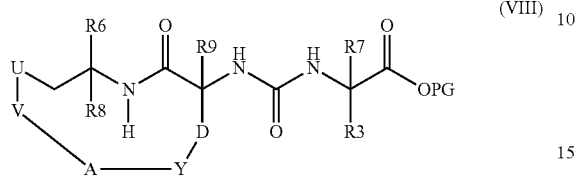

(VIII)

and subsequently eliminating the protective group PG and the protective group which is present where appropriate on the nitrogen in R3, resulting in the compound of the formula (I), or b) reacting a compound of the formula (IX)

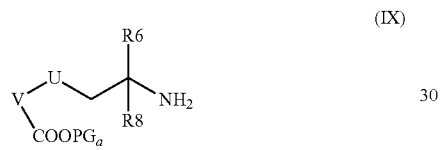

(IX)

in which U, V, R6 and R8 have the meanings mentioned in the compound of the formula (I), and $PG_a$ is a suitable carboxyl protective group, with an amino acid of the formula (X)

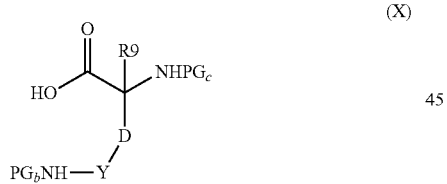

(X)

in which R9, Y and D have the meanings mentioned in the compound of the formula I, and $PG_b$ and $PG_c$ are suitable amino protective groups, resulting in a compound of the formula (XI)

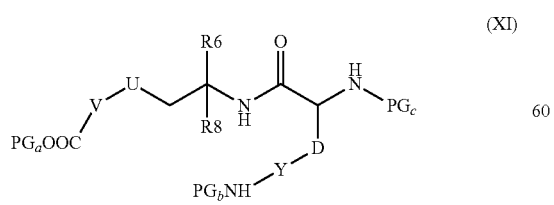

(XI)

and eliminating the protective groups $PG_a$ and $PG_b$, to result in a compound of the formula (XII)

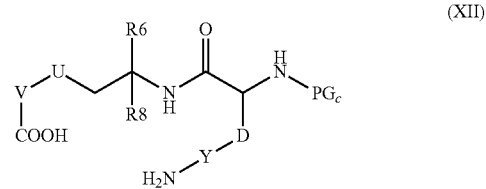

(XII)

and converting the compound of the formula (XII) by means of amide coupling into a compound of the formula (V), in which A has the meanings mentioned in the compound of the formula I, subsequently eliminating the protective group resulting in the compound of the formula (VI), and reacting the compound of the formula (IV) with a compound of the formula (VII)

in which R3 and R7 have the meanings mentioned in formula I, PG is a suitable ester protective group radical, and the nitrogen in R3 is protected where appropriate by a suitable amino protective group, with phosgene or a phosgene equivalent to give a compound of the formula (VIII), and subsequently eliminating the protective group PG and the protective group which is present where appropriate on the nitrogen in R3 resulting in the compound of the formula (I), or c) reacting a compound of the formula (XIII)

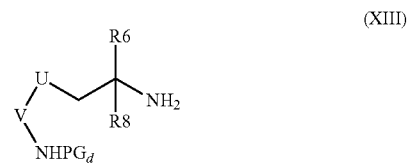

(XIII)

in which U, V, R6 and R8 have the meanings mentioned in the compound of the formula I, and $PG_d$ is a suitable amino protective group, with an amino acid of the formula (XIV)

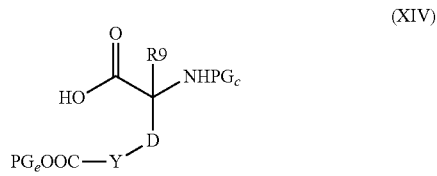

(XIV)

in which R9, Y and D have the meanings mentioned in the compound of the formula I, and $PG_c$ is a suitable amino protective group and $PG_e$ is a suitable carboxyl protective group, resulting in a compound of the formula (XV)

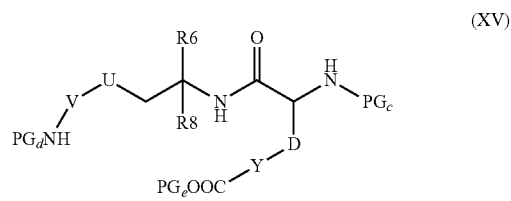

(XV)

and eliminating the protective groups PG$_d$ and PG$_e$, to result in the compound of the formula (XVI)

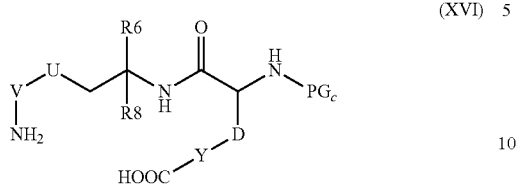
(XVI)

and reacting the compound of the formula (XVI) to give a compound of the formula (V), in which A has the meanings mentioned in the compound of the formula I, and subsequently eliminating the protective group resulting in the compound of the formula (VI), and reacting the compound of the formula (VI) with a compound of the formula (VII), in which R3 and R7 have the meanings mentioned in formula I, PG is a suitable ester protective group radical, and the nitrogen in R3 is protected where appropriate by a suitable amino protective group, with phosgene or a phosgene equivalent to give a compound of the formula (VIII), and subsequently eliminating the protective group PG and the protective group which is present where appropriate on the nitrogen in R3, resulting in the compound of the formula (I), or d) reacting a compound of the formula XVII

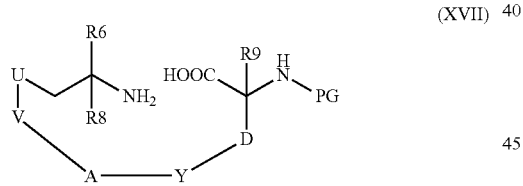
(XVII)

in which U, V, A, Y, D, R$_6$, R$_8$ and R$_9$ have the meanings mentioned in the compound of the formula I, with a compound of the formula (V), and subsequently eliminating the protective groups to result in a compound of the formula (VI), and reacting the compound of the formula (VI) with a compound of the formula (VII), in which R3 and R7 have the meanings mentioned in formula I, PG is a suitable ester protective group radical, and the nitrogen in R3 is protected where appropriate by a suitable amino protective group, with phosgene or a phosgene equivalent to give a compound of the formula (VIII), and subsequently the protective groups PG and, where appropriate, eliminating the protective group on the nitrogen in R3, resulting in the compound of the formula (I), or e) converting a compound of the formula (VIIIa)

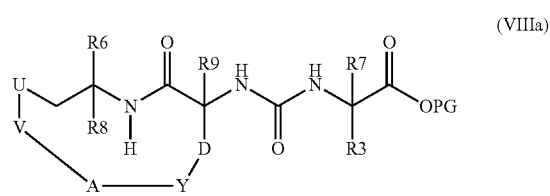
(VIIIa)

in which V is —(C$_3$-C$_9$)-alkenylene-, into the compound of the formula (VIIIb)

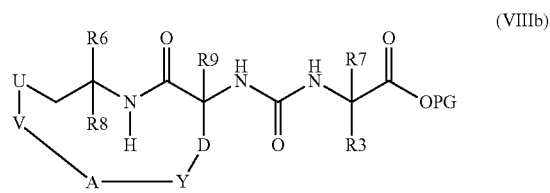
(VIIIb)

in which V is —(C$_3$-C$_9$)-alkylene-, where alkylene is substituted independently of one another once, twice or three times by —OH, NH$_2$ or halogen, or is —(C$_1$-C$_2$)-alkylene-(C$_3$-C$_6$)-cycloalkyl-(C-C$_2$)-alkylene-, where cycloalkyl is substituted independently of one another once, twice or three times by R15, and subsequently eliminating the protective group PG and the protective group which is present where appropriate on the nitrogen in R3, resulting the compound of the formula (I), or f) reacting a compound of the formula (XVIII)

(XVIII)

in which V is as defined in the compound of the formula (I), successively with the compounds of the formula (XIX) and (XX)

(XIX)

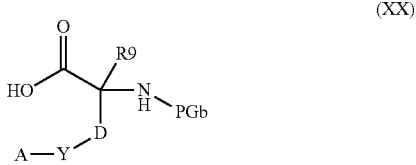
(XX)

employing bases in polar, aprotic solvents, and converting the resulting compounds of the formula (XXI)

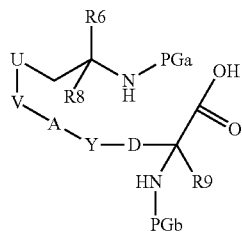

(XXI)

by removing the protective group PGa and subsequently forming of a peptide linkage into a compound of the formula (V), and reacting the resulting compound of the formula (V) as in process a) to give compounds of the formula (I) in which R6, R8, R9, and A, D, U, V and Y have the meanings mentioned in formula (I), and PG is suitable protective groups, and LG is a leaving group such as chlorine, bromine, iodine or sulfonic ester, or g) reacting a compound of the formula (VI) with a compound of the formula (XXII)

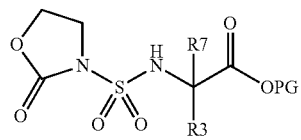

(XXII)

in which R3 and R7 have the meanings mentioned in the compound of the formula (I), and PG is a suitable protective group radical, to give a compound of the formula (XXIII)

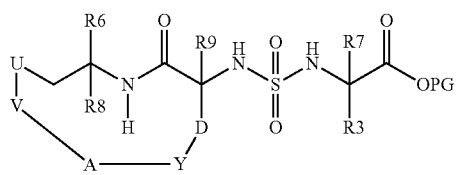

(XXIII)

and converting the compound of the formula (XXIII) into a compound of the formula (I), or h) fractionating a compound of the formula (I) prepared by processes a), b), c), d), e), f) or g), or a suitable precursor of the formula (I) which occurs in enantiomeric forms owing to its chemical structure, by salt formation with enantiopure acids or bases, chromatography on chiral stationary phases or derivatization by means of chiral enantiopure compounds such as amino acids, separation of the diastereomers obtained in this way, and elimination of the chiral auxiliary groups into the pure enantiomers, or i) either isolating in free form the compound of the formula (I) prepared by processes a), b), c), d), e), f) or g), or converting into physiologically tolerated salts in the case where acidic or basic groups are present.

5. A medicament comprising an effective content of at least one compound of the formula I as claimed in claim 1, or a physiologically tolerated salt thereof together with a pharmaceutically suitable and physiologically tolerated carrier, additive and/or other active ingredients and excipients.

6. A method for the therapy of one or more disorders which are associated with thromboses, embolisms, hypercoaguability or fibrotic changes comprising administering a therapeutically effective amount of a compound according to claim 1, or a physiologically tolerated salt thereof, to a patient in need of such treatment.

7. The method according to claim 6, wherein the disorders are selected from the group consisting of myocardial infarction, angina pectoris, acute coronary syndrome, stroke, peripheral vascular disorders, deep vein thrombosis, pulmonary embolism, embolic or thrombotic events caused by cardiac arrhythmias, and restenosis following revascularization, angioplasty, stent implantation or bypass operations.

8. A method for reducing the risk of thrombosis formation following surgical procedures comprising administering a therapeutically effective amount of a compound according to claim 1, or a physiologically tolerated salt thereof, to a patient in need of such treatment.

9. The method according to claim 8 wherein the surgical procedure is selected from the group consisting of knee replacement surgery and hip replacement surgery.

10. A method for the therapy of disseminated intravascular coagulation, sepsis or intravascular events associated with inflammation comprising administering a therapeutically effective amount of a compound according to claim 1, or a physiologically tolerated salt thereof, to a patient in need of such treatment.

11. A method for the therapy of atherosclerosis, tumor growth and metastasis, inflammatory and degenerative articular disorders, diabetes or metabolic syndrome and the sequelae thereof comprising administering a therapeutically effective amount of a compound according to claim 1, or a physiologically tolerated salt thereof, to a patient in need of such treatment.

12. The method according to claim 11 wherein the articular disorder is chosen from the group consisting of rheumatoid arthritis and arthrosis.

13. A method for the therapy for impairments to the hemostatic system comprising administering a therapeutically effective amount of a compound according to claim 1, or a physiologically tolerated salt thereof, to a patient in need of such treatment.

14. The method according to claim 13 wherein said impairment to the hemostatic system is fibrin deposition.

15. A method for the therapy of chronic obstructive pulmonary disease, adult respiratory distress syndrome, fibrin deposits in the eye following eye operations or the prevention or treatment of scarring of the eye comprising administering a therapeutically effective amount of a compound according to claim 1, or a physiologically tolerated salt thereof, to a patient in need of such treatment.

* * * * *

UNITED STATES PATENT AND TRADEMARK OFFICE
CERTIFICATE OF CORRECTION

| | | |
|---|---|---|
| PATENT NO. | : 9,126,955 B2 | Page 1 of 3 |
| APPLICATION NO. | : 14/226132 | |
| DATED | : September 8, 2015 | |
| INVENTOR(S) | : Christopher Kallus et al. | |

It is certified that error appears in the above-identified patent and that said Letters Patent is hereby corrected as shown below:

On the Title Page:

Right column, under OTHER PUBLICATIONS, lines 23-25: please replace "Thrombin-Activatable Fibrinolysis Inhibitor (TAFI, Plasma Procarboxypeptidase B, Procarboxypeptidase R, Procarboxypeptiase U)" with --Thrombin-Activatable Fibrinolysis Inhibitor (TAFI, Plasma Procarboxypeptidase B, Procarboxypeptidase R, Procarboxypeptidase U)--;

Right column, under OTHER PUBLICATIONS, line 29: please replace "(1994(" with --(1994)--;

On the second page, left column, under OTHER PUBLICATIONS, line 17: please replace "Product Class 8: Acyclic and Cycli Ureas" with --Product Class 8: Acyclic and Cyclic Ureas--.

In the Claims:

At column 50, claim number 1, lines 19-28: please replace

"V is
—$(C_2-C_9)$-alkylene-, where alkylene is unsubstituted or
    substituted independently of one another once, twice or
    three times by —OH, $NH_2$ or halogen,
D is —$(C_1-C_2)$-alkylene-,
Y is
phenyl, where phenyl is unsubstituted or substituted inde-
    pendently of one another once, twice or three times by
    R15,
R1 is"

Signed and Sealed this
Twenty-first Day of June, 2016

Michelle K. Lee
*Director of the United States Patent and Trademark Office* with

--V is —$(C_2-C_9)$-alkylene-, where alkylene is unsubstituted or substituted independently of one another once, twice or three times by —OH, NH$_2$ or halogen,
D is —$(C_1-C_2)$-alkylene-,
Y is phenyl, where phenyl is unsubstituted or substituted independently of one another once, twice or three times by R15,
R1 is--;

At column 51, claim number 1, lines 27-28: please replace

"R16 is —O—CF$_3$, —NH$_2$, —OH, —CF$_3$ or halogen; or a physiologically tolerated salt thereof."

with

--R16 is —O—CF$_3$, —NH$_2$, —OH, —CF$_3$ or halogen; or a physiologically tolerated salt thereof.--;

At column 51, claim number 2, lines 33-34: please replace

"V is —$(C_2-C_9)$-alkylene-, wherein the alkylene is unsubstituted"

with

--V is —$(C_2-C_9)$-alkylene-, wherein the alkylene is unsubstituted,--;

At column 51, claim number 3, lines 39-41: please replace "(S)-6-amino-2((8S,11R)-8-isopropyl-3,10-dioxo-6-oxa-2,9-diazabicyclo[11.2.2]heptadeca-1(16),13(17),14-trien-11-ylamino)hexanoic acid" with --(S)-6-amino-2-((8S,11R)-8-isopropyl-3,10-dioxo-6-oxa-2,9-diazabicyclo[11.2.2]heptadeca-1(16),13(17),14-trien-11-ylamino)hexanoic acid--;

At column 51, claim number 3, lines 42-44: please replace "(S)-3-(6-aminopyridin-3-yl)-2-((8S,11R)-8-methyl-3,10-dioxo-6-oxa-2,9diazabicyclo [11.2.2]heptadeca-1(16),13(17),14-trien-11-yl)ureido] propionic acid" with --(S)-3-(6-aminopyridin-3-yl)-2-[3-((8S,11R)-8-methyl-3,10-dioxo-6-oxa-2,9-diazabicyclo[11.2.2]heptadeca-1(16),13(17),14-trien-11-yl)ureido]propionic acid--;

CERTIFICATE OF CORRECTION (continued)
U.S. Pat. No. 9,126,955 B2

At column 51, claim number 3, lines 45-47: please replace "(S)-3-(6-aminopyridin-3-yl)-2-[3-((8S,11R)-8-isopropyl-2,10-dioxo-6-oxa-3,9diazabicyclo[11.2.2]heptadeca-1(16),13(17),14-trien-11-yl)ureido]propionic acid" with --(S)-3-(6-aminopyridin-3-yl)-2-[3-((8S,11R)-8-isopropyl-2,10-dioxo-6-oxa-3,9-diazabicyclo[11.2.2]heptadeca-1(16),13(17),14-trien-11-yl)ureido]propionic acid--; and At column 51, claim number 3, lines 49-51: please replace "(S)-6-Amino-2-[3-((8S,11R)-8-isopropyl-3,10-dioxo-6-oxa-2,9diazabicyclo[11.2.2]heptadeca-1(16),13(17),14-trien-11-yl)ureido]hexanoic acid" with --(S)-6-Amino-2-[3-((8S,11R)-8-isopropyl-3,10-dioxo-6-oxa-2,9-diazabicyclo[11.2.2]heptadeca-1(16),13(17),14-trien-11-yl)ureido]hexanoic acid--.